(12) United States Patent
Sholl et al.

(10) Patent No.: US 6,874,000 B2
(45) Date of Patent: Mar. 29, 2005

(54) SYSTEM AND METHOD FOR IDENTIFYING A FOOD EVENT, TRACKING THE FOOD PRODUCT, AND ASSESSING RISKS AND COSTS ASSOCIATED WITH INTERVENTION

(75) Inventors: Jeffrey John Sholl, Minnetonka, MN (US); Andrew Martin Jaine, Rancho Santa Fe, CA (US); Susan Kay Harlander, New Brighton, MN (US)

(73) Assignee: Food Security Systems, LLC, Minnetonka, MN (US)

( * ) Notice: Subject to any disclaimer, the term of this patent is extended or adjusted under 35 U.S.C. 154(b) by 0 days.

(21) Appl. No.: 10/681,581

(22) Filed: Oct. 8, 2003

(65) Prior Publication Data

US 2004/0083201 A1 Apr. 29, 2004

Related U.S. Application Data
(60) Provisional application No. 60/417,099, filed on Oct. 8, 2002, and provisional application No. 60/469,875, filed on May 12, 2003.

(51) Int. Cl.[7] .............................................. G06F 7/00
(52) U.S. Cl. ................................... 707/104.1; 706/924
(58) Field of Search ..................... 707/104.1; 706/924; 235/375–386; 705/2–4

(56) References Cited

U.S. PATENT DOCUMENTS

| | | | | |
|---|---|---|---|---|
| 5,478,990 | A | * 12/1995 | Montanari et al. | 235/375 |
| 6,409,082 | B1 | * 6/2002 | Davis et al. | 235/385 |
| 6,671,698 | B2 | * 12/2003 | Pickett et al. | 707/104.1 |
| 6,691,135 | B2 | * 2/2004 | Pickett et al. | 707/104.1 |
| 2003/0018513 | A1 | * 1/2003 | Hoffman et al. | 705/10 |
| 2003/0069774 | A1 | * 4/2003 | Hoffman et al. | 705/8 |
| 2003/0074250 | A1 | * 4/2003 | Burk | 705/10 |
| 2003/0083947 | A1 | * 5/2003 | Hoffman et al. | 705/22 |
| 2003/0177025 | A1 | * 9/2003 | Curkendall et al. | 705/1 |
| 2004/0078227 | A1 | * 4/2004 | Morris | 705/2 |

FOREIGN PATENT DOCUMENTS

| | | | |
|---|---|---|---|
| WO | WO 01/35376 | 5/2001 | ........... G09B/19/00 |
| WO | WO 03/048725 A2 | 6/2003 | |
| WO | WO 03/098388 A2 | 11/2003 | |

OTHER PUBLICATIONS

International Commission on Microbiological Specifications for Foods (ICMSF) "Microorganisms in Foods, vol. 4", Oxford:Blackwell Scientific Publications, pp. 1–43 and 207–263, 1988. ISBN 0–632–02181–0. QR115.I46 1988.*
Zwietering, M.H. et al. "Modeling of Bacterial Growth as a Function of Temperature", Applied and Environmental Microbiology, pp. 1094–1101, Apr. 1991.*
Zwietering, M.H. et al. "A Decision Support System for Prediction of the Microbial Spoilage of Foods", Journal of Food Protection, vol. 55, No. 12, pp. 973–979, Dec. 1992.*
Gorris, L.G.M. and M.W. Peck "The Food Micromodel for Prediction of Growth of Foodborne Pathogens", Voedingsmiddelentechnologie, vol. 26, No. 5, pp. 36–39, 1993 (Abstract Only).*

(Continued)

Primary Examiner—Luke S Wassum
(74) Attorney, Agent, or Firm—Westman, Champlin & Kelly, P.A.

(57) ABSTRACT

The food safety system and method of the present invention provides a comprehensive consumer risk distribution model, which can be applied to any food item. Additionally, the present invention automatically evaluates consumer risk based on how much contaminated food is at each stage of the food distribution process according to the consumer risk distribution model, allowing for quick and accurate determinations as to the efficacy of a trace recall effort. A further element of the present invention provides expert analysis of data to detect and identify food events from sporadic information. Finally, the real time detection system provides early warning data in order to intercept isolated food contamination events before the contaminated food products reach the consuming public.

14 Claims, 29 Drawing Sheets

OTHER PUBLICATIONS

Lammerding, A.M. and G.M. Paoli "Quantitative Risk Assessment: An Emerging Tool for Emerging Foodborne Pathogens", Emerging Infectious Diseases, vol. 3, pp. 483–487, Oct./Dec. 1997.*

Wijtzes, T. et al. "A Decision Support System for the Prediction of Microbial Food Safety and Food Quality", International Journal of Food Microbiology, vol. 42, pp. 79–90, 1998.*

Food Safety and Inspection Service "Salmonella Enteritidis Risk Assessment: Shell Eggs and Egg Products", Final Report, available at www.fsis.usda.gov/OPHS/risk/, Aug. 10, 1998.*

Bidawid, S., J.M. Farber and S.A. Sattar "Contamination of Foods by Food Handlers: Experiments on Hepatitis A Viral Transfer to Food and Its Interruption", Applied and Environmental Microbiology, vol. 66, No. 7, pp. 2759–2763, Jul. 2000.*

Bailar, J.C. III "Ensuring Safe Food: An Organizational Perspective", in Layne, S.P. et al., eds. "FirePower in the Lab: Automation in the Fight Against Infectious Diseases and Bioterrorism", Washington, DC:Joseph Henry Press, NAS, pp. 133–142 2000.*

Maslanka, S.E. et al. "Foodborne Pathogen and Toxin Diagnostics", in Layne, S.P. et al., eds. "FirePower in the Lab: Automation in the Fight Against Infectious Diseases and Bioterrorism", Washington, DC:Joseph Henry Press, NAS, pp. 143–163 2000.*

FoodNet Annual Report 2000, published 2001.*

Kleer, J. and G. Hildebrandt "Importance of Predictive Microbiology for Risk Minimization in Food Production Processes", Fleischwirtschaft, vol. 81, No. 6, pp. 99–103, 2001. (Abstract Only).*

Koopman, J. "Responding to an Infection Transmission Emergency", PowerPoint™ presentation, IMA Special "Hot Topics" Workshop: Operational Modeling and BioDefense: Problems, Techniques and Opportunities, Sep. 28, 2002.*

Scott, J. and R.S. Applebaum "The Food Industry's Response to Ensuring Food Security and Safety", PowerPoint™ presentation, Bioterrorism and Food Security: Issues and Challenges, Oct. 28–19, 2002.*

Cipra, B.A. "'Hot Topics' Workshop Takes a Logistical Look at Biodefense", SIAM News, vol. 35, No. 10, Dec. 2002.*

National Research Council "Making the Nation Safer: The Role of Science and Technology in Countering Terrorism", Committee on Science and Technology for Countering Terrorism, Washington, DC:National Academies Press, 2002. ISBN 0–309–08481–4 HV6431.M354.*

Woo, G. "The Evolution of Terrorism Risk Modeling", Journal of Reinsurance, London, England, Apr. 22, 2003.*

Bruemmer, B. "Food Biosecurity", Journal of the American Dietetic Association, vol. 103, No. 6, pp. 687–691, Jun. 2003.*

Nganje, W., W.W. Wilson and J. Nolan "Terrorism and the Grain Handling System in Canada and the United States", Canadian Agricultural Economics Society Annual Meeting, Jul. 26–30, 2003.*

Joppen, L. "Food Terror", Food Engineering & Ingredients, vol. 28, No. 4, p. 3, Aug. 2003.*

Food Safety and Inspection Service "Quantitative Assessment of the Relative Risk to Public Health from Foodborne Listeria monocytogenes Among Selected Categories of Ready–to–Eat Foods", Center for Food Safety and Applied Nutrition, Sep. 2003.*

Lambert, C. "Agroterrorism: The Threat to America's Breadbasket", Statement before the Senate Committee on Governmental Affairs, available from http://govt–aff.senate.gov, Nov. 19, 2003.*

Murano, E. "Perspectives on Food Security", speech presented by the Under Secreatry for Food Safety at the Amarillo Farm and Ranch Show, Amarillo, Texas, U.S. Department of Agriculture, available from http://www.fsis.usda.gov, Dec. 2, 2003.*

American Association for the Advancement of Science "Planning Effective Bioterror Responses", press release, Feb. 14, 2004.*

Golan, E. et al., "Traceability in the U.S. Food Supply: Economic Theory and Industry Studies", U.S. Department of Agriculture Economic Research Service, Agricultural Economic Report No. 830, Mar. 2004.*

Sholl, J. "Security of the Food Supply: Detection, Identification and Response", PowerPoint™ presentation, Apr. 22, 2004.*

Centers for Disease Control (CDC) "What is FoodNet?", available at http://www.cdc.gov/foodnet, Aug. 2004.*

National Academy of Sciences "Countering Agricultural Bioterrorism", available at http://books.nap.edu/catalog/10505.html, executive summary only, 2004.*

Zebra Technologies "Bar Coding and RFID: The Key to Traceability and Safety in the Foodservice Supply Chain", white paper, 2004.*

U.S. Department of Agriculture National Inter–Agency Incident Management System (NIIMS): Operational System Description 2004.*

Labuza, T. "Food Bio–Security: Case Studies in the Food Distribution Chain", PowerPoint™ presentation, Department of Food Science and Nutrition, University of Minnesota, 2004.*

Cellarosi, G. et al., *Detecting Outbreaks by Time Series Analysis*, $15^{th}$ IEEE Symposium on Computer–Based Mecial Systems (CBMS 2002), Jun. 4–7, 2002, pp. 159–164.

"Making the Nation Safe: The Role of Science and Technology in Countering Terrorism," Committee on Science and Technology for Countering Terrorism, National Research Council, National Academies Press, Washington, D.C. 2002, pp. 1–106.

Cipra, Barry A.; "Hot Topics" Workshop Takes a Logistical Look at Biodefense from SIAM News, vol. 35, No. 10, Dec. 2002, pp. 1–3.

Cellarosi et al., G.; "Detecting Outbreaks by Time Series Analysis," Dept. of Electronics, Computer Science and Systems, Proceedings of the 15th IEEE Symposium on Computer–Based Medical Systems, 2002, pp. 1–6.

Scott, J. and Applebaum, R.; "The Food Industry's Response to Ensuring Food Security and Safety," Bioterrorism and Food Security: Issues and Challenges, National Food Processors Association, Oct. 28–29, 2002, 50 pages.

Copy of International Search Report of US PCT Receiving Office.

Quantitative Assessment of the Relative Risk to Public Health from Foodborne *Listeria monocytogenes* Among Selected Categories of Ready–to–Eat Foods, Center for Food Safety and Applied Nutrition Food and Drug Administration, U.S. Department of Health and Human Services, Sep. 2003, pp. 1–272.

Woo, Dr. Gordon.; "The Evolution of Terrorism Risk Modeling," *Journal of Reinsurance,* Apr. 22, 2003, 9 pgs.

Nganje et al., W.; "Terrorism and the Grain Handling System in Canada and the United States," Principal Session 2, Paper 3, CAES Annual Meeting, Jul. 26–30, 2003, Montreal Canada. *Journal of Canadian Agricultural Economics Society,* pp. 1–35.

Abstract Only : Wijtzes et al., T.; "A Decision Support System for the Predicition of Microbial Food Safety and Food Quality," *International Journal of Food Microbiology,* vol. 42, Issue 1–2, Jun. 30, 1998, pp. 79–90.

Bailar III, J.; "Ensuring Safe Food: An Organizational Perspective," *FirePower in the Lab,* Joseph Henry Press, Washington D.C., 2001. pp. 133–142.

Maslanka et al., S.; "Foodborne Pathogen and Toxin Diagnostics: Current Methods and Needs Assessment from Surveillance, Outbreak Response, and Bioterrorism Preparedness Perspectives," *FirePower in the Lab,* Joseph Henry Press, Washington D.C., 2001. pp. 143–163.

Bruemmer, B.; "Food Biosecurity," *Journal of the American Dietetic Association,* vol. 103, No. 6, Jun. 2003. pp. 687–692

Lammerding, A.M. and Paoli, G.M.; "Quantitative Risk Assessment: An Emerging Tool for Foodborne Pathogens," *Emerging Infectious Diseases,* vol. 3 (Oct./Dec. 1997, pp. 483–487.

Joppen, L.; "Food Terror," *Food Engineering and Ingredients,* vol. 28, No. 4, Aug. 2003, p. 3.

Bidawid et al., S.; "Contamination of Foods by Food Handlers: Experiments on Hepatitis A Virus Transfer to Food and Its Interruption" *Applied and Environmental Microbiology,* vol. 66, No. 7, Jul. 2000, pp. 2759–2763.

Food Net Annual Report 2000, Published 2001. Pp. 1–36.

Koopman, J.; "Responding to an Infection Transmission Emergency," IMA Special "Hot Topics" Workshop: Operational Modeling and Biodefense, Problems, Techniques and Opportunities. University of Minnesota Institute for Mathematics and Its Applications. 16 pgs.

* cited by examiner

FIG. 8

Food Safety Systems Analytical Model

Analytical Predictive Modeling Tool ("APMT")

Please select the type of incident to be modeled by clicking the appropriate button below.

| Unintentional Contamination | Intentional Contamination |
|---|---|

FIG. 9

Food Safety Systems Analytical Model

Analytical Predictive Modeling Tool ("APMT")

Please select the type of incident to be modeled by clicking the appropriate button below.

| Unintentional Contamination | Intentional Contamination |
|---|---|

Scenario: Unintentional

To run the model, please select the desired criteria by clicking on the dropdown boxes below, then click "Run"

- Contaminant: C. Botulinum Toxin — 74A
- Food: Milk — 74B
- Contaminant Point: Tanker Truck — 74C
- Contaminated Product Quantity (Enter quantity or click button to select): 4,500 gallons — 74D
- Season: Spring — 74E
- Public Health Response Time (Enter time in days or click button to select): Normal Response — 74F

[ Run ] — 76

*← 70*

```
┌─ Food Safety Systems Analytical Model ─────────── _ □ × ┐
│                                                         │
│         Analytical Predictive Modeling                  │
│                 Tool ("APMT")                           │
│       Please select the type of incident to be modeled  │
│           by clicking the appropriate button below.     │
│        ┌──────────────┐    ┌──────────────┐             │
│        │ Unintentional│    │  Intentional │  ◄── 72     │
│        │ Contamination│    │ Contamination│             │
│        └──────────────┘    └──────────────┘             │
│              Scenario: Unintentional                    │
│        To run the model, please select the desired      │
│        criteria by clicking on the dropdown boxes       │
│                below, then click "Run"                  │
│                                                         │
│                 Agent  [ C. Botulinum Toxin ▼]  ⎫       │
│                  Food  [ Milk               ▼]  ⎪       │
│      Contaminant Point [ Tanker Truck       ▼]  ⎬ 74    │
│  Contaminated Product Quantity [ 45,000 gallons ▼] ⎪    │
│    Enter quantity or click button to select     ⎪       │
│                Season  [ Spring             ▼]  ⎪       │
│        Agency Reponsce Time  [ 6 days       ▼]  ⎭       │
│    Enter time in days or click button to select         │
│                                                         │
│                   ┌──────────────┐                      │
│                   │     Run      │ ── 76                │
│                   └──────────────┘                      │
└─────────────────────────────────────────────────────────┘
```

SYSTEM AND METHOD FOR IDENTIFYING A FOOD EVENT, TRACKING THE FOOD PRODUCT, AND ASSESSING RISKS AND COSTS ASSOCIATED WITH INTERVENTION

CROSS-REFERENCE TO RELATED APPLICATION(S)

This application claims priority from provision application Ser. No. 60/417,099, filed on Oct. 8, 2002 and entitled "FOOD SAFETY SYSTEM AND METHOD", which is incorporated herein by reference. This application also claims priority from application Ser. No. 60/469,875, filed on May 12, 2003, and entitled "SYSTEM AND METHOD FOR IDENTIFYING, TRACING AND RECALLING CONTAMINATED FOOD ITEMS", which is also incorporated herein by reference.

BACKGROUND OF THE INVENTION

The present invention relates to bacterial and microbial contamination of food items. More particularly, the present invention relates to a system and method for identifying contaminated food products, tracing the contaminated food products within the food distribution chain, and facilitating actions such as recalling contaminated food items and alerting consumers through various media.

For the purpose of this invention, the term "pollutants" refers to toxins, harmful bacteria (such as *e-coli, Coxiella burnetti, botulinum, thermosaccharolyticum,* and the like), pathogens, contaminants, organic agents, inorganic agents, radiological agents, radiological agents or any other non-beneficial agents that find their way into food products. The term "harmful" is used herein means deleterious to human health. Such pollutants may be naturally occurring, maybe the result of a contamination event (such as introduction of the food product into a non-sterile environment), or may be the result of tampering with the food products (as when someone tampered with Tylenol brand of acetaminophen capsules in 1982).

Generally, much of the fresh food supply in the United States and around the world is perishable because of its moderate to high water content and because of its nutritious nature. The causes of deterioration in spoilage of food products include the growth of microorganisms (by far the most common cause), contamination (filth, absorption of odors, etc.), normal respiration (plant tissues), loss of water (sprouting), autolysis (especially fish), various chemical reactions such as oxidation, physiological disorders (such as scald of apples, cold shortening of muscle, chilling injury and anaerobic respiration of plant tissues), and mechanical damage (bruising, and the like).

Spoilage of perishable foods can be prevented only by prompt consumption, which often is not possible, or by prompt effective preservation. Effective preservation not only retards spoilage, but also helps reduce the possibility of contamination of the food product. The aim of commercial food preservation is to prevent undesirable changes in the wholesomeness, nutritive value, or sensory quality of food by economical methods which control growth of microorganisms, reduce chemical, physical, and physiological changes of an undesired nature, and obviate contamination.

Currently, preservation of food can be accomplished by chemical, biological, or physical means. Generally chemical preservation involves the addition to food of such substances as sugars, salts, or acids or exposure of food to chemicals such as smoke or fumigants. Biological preservation involves alcoholic or acidic fermentations. Physical approaches to preserving food include temporary increases in the products energy level (heating or irradiation), controlled reduction of the products temperature (chilling, freezing, and the like), controlled reduction in the products water content (concentration, air dehydration, freeze drying), and the use of productive packaging.

During preservation of moderately or highly perishable foods, the greatest concern is related to microorganisms. Physical methods of preservation result either in death of microorganisms (by temporarily increasing the energy level of a food which is suitably packaged to avoid recontamination), or suppression of their growth (by maintaining the food at sub-ambient temperatures or by removing water followed by packaging to avoid reabsorption of water).

Although certain physical methods of food preservation completely stop stop growth of microorganisms and greatly retard the rates of chemical reactions (and spoilage), it is important to recognize that none of these methods can completely prevent chemical and physical changes. For example, in frozen foods stored at a recommended temperature of 18 degrees celsius, microorganisms cannot grow, but degradation of vitamin C, insolubilization of protein, oxidation of lipids, and recrystallization can occur at significant rates. Additionally, methods of preservation that successfully stop the growth of microorganisms sometimes have undesirable consequences with respect to the sensory and nutritional attributes of food. For example, thermal sterilization softens food tissues, degrades chlorophyls and anthocyanins alters flavors, and results in loss or degradation of vitamins.

One method of preservation of food products is called pasteurization. Pasteurization is a heat treatment that kills part but not all of the vegetable microorganisms present in the food, and consequently it is used for foods which are to be further handled and stored under conditions which minimize microbial growth. In many cases, the primary objective of pasteurization is to kill pathogenic microorganisms. Some vegetative spoilage organisms can survive this heat treatment, and thus more severe preservation methods are needed if microbial spoilage is to be prevented. In other cases, such as in beer, pasteurization serves primarily to kill vegetative spoilage organisms. Other preservation techniques used in conjunction with pasteurization typically include refrigeration, chemical additives, packaging, and fermentation.

Pasteurization generally involves heating the food product to a specific temperature for a period of time. The time temperature treatment used in pasteurization depends upon the heat resistance of the particular vegetative or pathogenic microorganism that the process is designed to destroy, and the sensitivity of the product quality to heat. In milk pasteurization for example, the high temperature and short time method involves a comparatively high temperature for a short period of time (e.g., 161 degrees Fahrenheit for 15 seconds for milk), whereas the low temperature and long time procedure involves relatively low temperatures for longer periods of time (e.g., 145 degrees Fahrenheit for 30 minutes for milk). Optimization of the pasteurization process depends on the relative destruction rate of various microorganisms as compared to quality factors of the food product. For market milk, pasteurization conditions are based on the thermal destruction of *coxiella burnetti*, the ricketsia organism responsible for Q fever. For high acid fruits such as cherries, the pasteurization process is based on successful destruction of yeast or molds. For fermented beverages such as wine or beer, the pasteurization criteria involves the destruction of wild yeasts.

In milk for example, the low temperature long time pasteurization process is targeted toward a particular organism. However, even with such pasteurization, contamination by other pollutants may occur from time to time. Additionally, storage conditions may contaminate the stored milk or provide an ambient condition for the microorganisms to reconstitute. Consequently, contamination of food products by pollutants occurs from time to time. Typically such occurrences are evidenced by sporadic outbreaks of illness among consumers and by occasional recall efforts. Whether the contamination is caused by E coli in tainted ground beef, by ricin in potatoes, or by various other pollutants on various types of food products, it is desirable to identify food contamination events quickly, and to take steps to contain the spread of the contamination so that the consumer impact is minimized.

Generally, once a food contamination is identified, food producers have few options. The food producers can recall all of the food items, assess the risk of not recalling the contaminated items against the costs associated with the recall effort, publically announce the contamination through media outlets, and destroy remaining produce. Typically, food producers employ one or more of these option for each food contamination event. Wrong decisions not only cost money, but may also cost lives (particularly if a recall effort is not mounted quickly).

Unfortunately, it has been found that public announcements of food contamination events are generally not very effective in reaching consumers. Additionally, since food producers are independent, there is no centralized or nation wide system for handling food contamination events. In fact, at present there is no standard method for addressing food contamination events.

Additionally, before remediating the food contamination event through one of the options described above, it is important that the source of the contamination is accurately identified. A misidentification of source can be very costly to food producers and may allow more time for the contaminated food items to circulate and to be consumed before the correct identification is made. Additionally, due to concerns about competition, food processing companies are reluctant to share information about distributors, harvesters and the like. This makes it very difficulty for public health officials to trace food contamination events to the source. Thus, even when the cause of an illness is properly identified by public health officials, reaching the affected consumers, distributors and other people in the food distribution chain can be extremely difficult.

BRIEF SUMMARY OF THE INVENTION

The food safety system and method of the present invention provides a comprehensive consumer risk distribution model, which can be applied to any food item. Additionally, the present invention automatically evaluates consumer risk based on how much contaminated food is at each stage of the food distribution process according to the consumer risk distribution model, allowing for quick and accurate determinations as to the efficacy of a trace recall effort. A further element of the present invention provides expert analysis of data to detect and identify food events from sporadic information. Finally, the real time detection system provides early warning data in order to intercept isolated food contamination events before the contaminated food products reach the consuming public.

BRIEF DESCRIPTION OF THE DRAWINGS

FIG. 8 is a screen shot of a first screen of the user interface of an embodiment of the present invention.

FIG. 9 is a screen shot of the user interface for an Unintentional Food Incident set up screen of the modeling system.

FIG. 10 is a screen shot of the user interface for an Intentional Food Incident set up screen of the modeling system.

FIGS. 11–29 are screen shots of the food incident profile tab at various stages within a model of a food contamination incident, modeling how an outbreak might progress over time.

Figure 1:
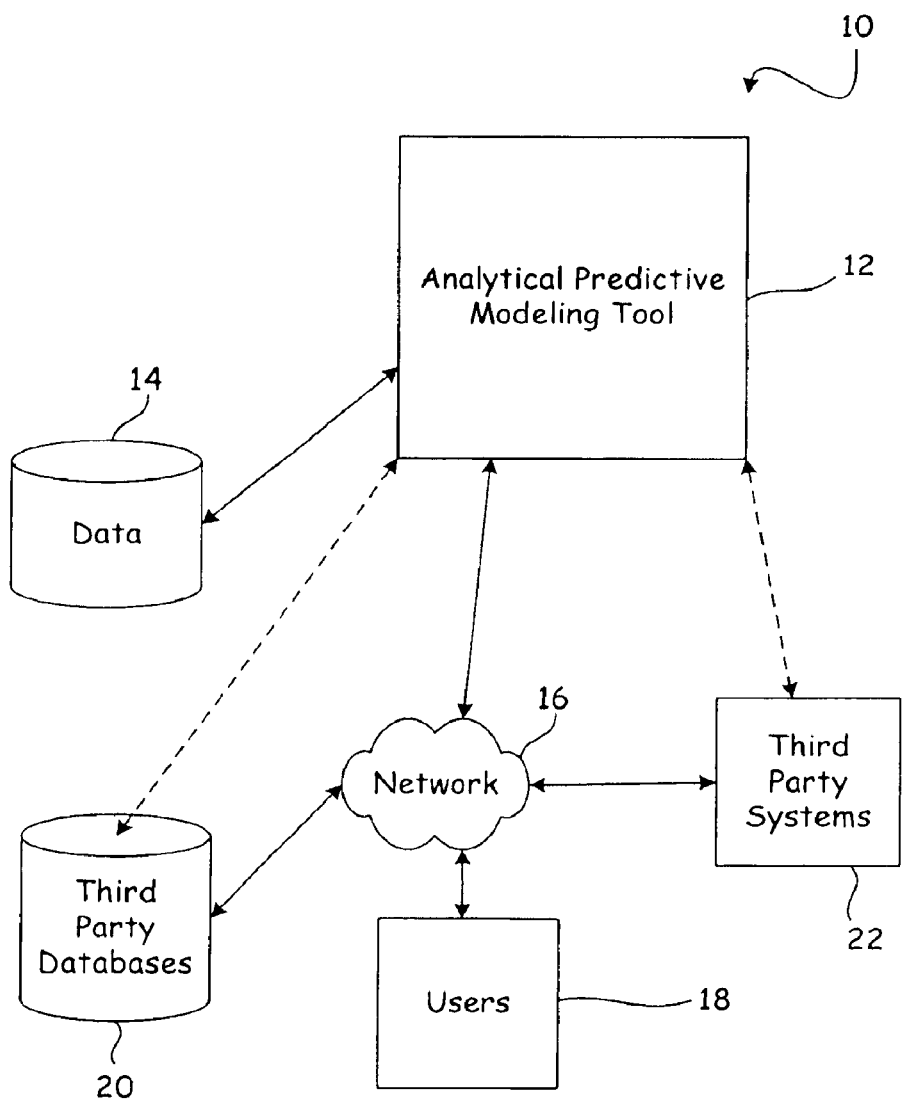
FIG. 1 is a block diagram of the system of the present invention.

While the above-identified illustrations set forth preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

Fresh food products have a very short usable life-cycle from packaging to spoilage. Typically, fresh foods become unusable in a matter of days or weeks. By contrast, pharmaceuticals, canned goods and other consumables typically enjoy a much longer shelf life, and the time from packaging to consumption of those goods may be many months.

Because of this short "life-cycle", fresh foods are packaged, sold, and consumed more rapidly than most other products. The rapidity of the consumption of fresh foods makes it difficult to identify, trace and recall food products before people are affected. Specifically, it takes several days for infected consumers to seek medical attention for contaminated food-related health problems. During that time, contaminated food has been purchased and consumed by many other individuals. By the time the contaminant is identified and the contaminated food is traced to the source, it is often times too late to effectively recall a product, in part, because the vast majority of the contaminated product has already been consumed or thrown away.

The present invention is a system and method for responding to a food contamination incident. Specifically, the present system combines product distribution profiles for each individual food product with food consumption and demographic data and with contaminant profiles. The system is used to effectively model a food contamination event by tracing food production from harvest through consumption in order to accurately estimate the consumer exposure to the food event. The system models consumer illness reporting and public health response times associated with food contamination event, either based on user input information or available historical data. The system provides context specific remediation options (such as public announcements, trace recall, and other interventions) and evaluates related costs directly attributable to the food event and to selected interventions. Finally, the system interfaces with trade associations, fresh food producers, and other players in the food distribution chain in order to trace contaminated produce backward and forward for effective containment and recall efforts. In essence, the system provides a "one-stop" user interface for tracking, assessing, and remediating food contamination events.

While the system and method discussed herein is directed to an overall strategy for food tracking, for simplicity, the majority of the discussion is directed to an embodiment of the invention, including screen shots from within a particular software implementation. The present invention is intended to be used by food suppliers, for the purpose of effective and quantifiably justified remediation decisions, as well as by public health officials for the purpose of determining the efficacy of particular intervention strategies, when a food contamination event has been detected.

Generally, the present invention serves as an analytical predictive modeling tool, coupled with the data required to support its predictive abilities. The modeling tool is designed to facilitate a qualitative analysis of product contamination events, based on seasonal food distribution profiles, statistical data, and collected demographic information. In particular, the present tool allows for iterative predictive modeling of probable outcomes and costs associated with different control and intervention approaches to food contamination events. The modeling tool accommodates the incorporation of a variety of assumptions about the nature of the threat and the effectiveness of the control and intervention strategies.

Specifically, the analytical predictive modeling tool is capable of generating hypothetical permutations to food contamination events. The modeling tool can project outcomes and their probabilities in terms of the likely distribution of human illness or death and in terms of economic consequences, based on assumptions about the underlying food contamination event, even before the source and nature of the contamination is known. Finally, the analytical tool incorporates different methods, time and types of intervention, depending on the particular point or points in the food production and distribution chain at which the intervention is applied.

FIG. 1 shows a block diagram of the system 10 of the present invention. The system 10 includes an analytical and predictive modeling tool (APMT) 12 and database(s) 14 for storing the data necessary for predictive modeling, which are accessible by the APMT 12. The APMT 12 may be connected to a network 16. The network 16 can be any type of network, including a local area network, a wide-area network, a telephone network, the Internet, or any other type of network (wired or wireless). The APMT 12 can be accessed by one or more authorized users 18 over the network 16. Finally, the APMT 12 can interact with third party data 20 and other third party systems 22, either over the network 16 or via direct connections (shown in phantom) in order to supplement the capabilities of the APMT 12.

In particular, to the extend that third parties and/or food distributors and producers maintain data related to food consumption, food distribution, health data or other relevant information, the APMT 12 can interact with their systems. The APMT 12 can query third party databases 20 or interact with third party systems 22 via direct connections, virtual private network (VPN) connections, or any secure connection means or directly such as via a direct modem connection.

As shown, a user 18 can interact with the tool 12 over the network 16 in order to perform a qualitative analysis of product contamination events, based on food distribution profiles, statistical data, and collected demographic information stored in the databases 14. In particular, the tool 12 allows for iterative predictive modeling of probable outcomes and costs associated with different control and intervention approaches to food contamination events. The tool 12 accommodates the incorporation of a variety of assumptions about the nature of the threat and the effectiveness of the control and intervention strategies via a user interface (discussed with respect to later figures).

Specifically, the tool 12 is capable of generating hypothetical permutations to food contamination events. The tool 12 can project outcomes and their probabilities in terms of the likely distribution of human illness or death and in terms of economic consequences, based on assumptions about the underlying food contamination event, even before the source and nature of the contamination is known. Finally, the tool 12 incorporates different methods, time and types of interventions, depending on the particular state in the food production and distribution chain at which the intervention is applied.

In general, by interfacing with existing data systems and by providing a simple and accessible user interface, the system 10 provides a framework based on a range of simple principles for facilitating the smooth and efficient transfer of information relating to each stage of the food chain. More importantly, the system 10 provides a targeted and statistically verifiable model of food as it passes through the food distribution network to the consumer. The system 10 provides a practical framework for evaluating an evolving food event, for tracing contaminated food throughout the distribution chain, and for evaluating the human and economic costs of various intervention strategies.

Figure 2:
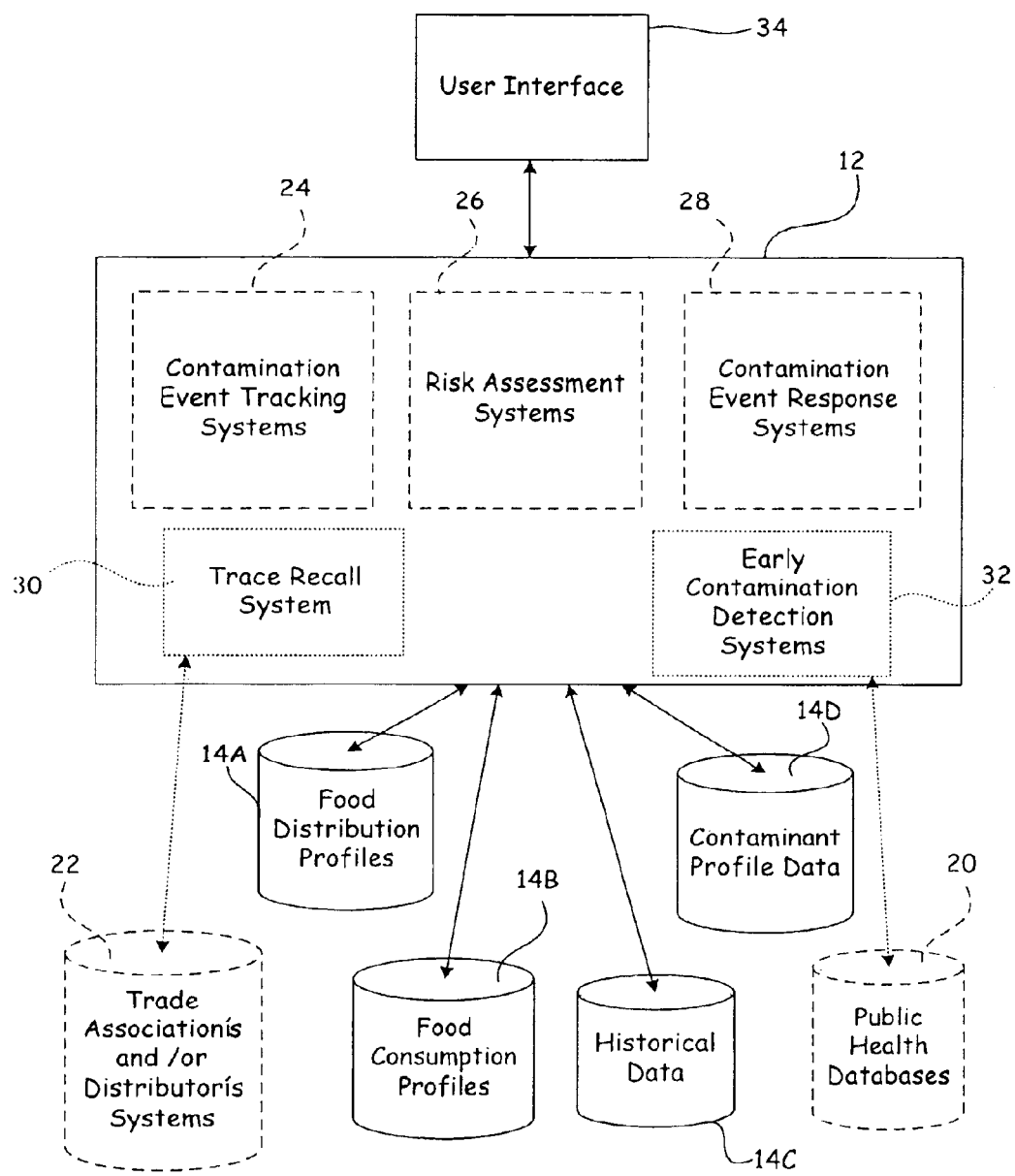
FIG. 2 is an expanded block diagram of the components of the system of FIG. 1.

FIG. 2 illustrates a block diagram of various elements of the system 10. As shown, the system 10 includes a contamination event tracking system 24, risk assessment system 26, contamination event response system 28, trace recall systems 30, and (optionally) early contamination detection systems 32. The contamination event tracking system 24, the risk assessment system 26 and the contamination event response system 28 utilize data stored in multiple databases, each of which may be multidimensional databases. As shown, the APMT 12 interacts with the food distribution profiles database 14A, the food consumption profiles database 14B, the historical food event profile database 14C, and a contaminant profile database 14D. Additionally, the trace recall systems 30 interact with multiple third party databases 22, such as various trade associations and/or distributor databases for the purpose of tracing contaminated food products within the distribution system.

Optionally, the system 10 may incorporate an early contamination detection system 32, which interacts with hospitals and public health officials located in areas at or near agricultural areas. For example, since a large percentage of lettuce produce is harvested from a small geographic area, health officials and hospitals in those areas can be monitored and/or plugged into the system 10 so that high incidence of illness from field workers and/or packing plant employees can provide a red flag for potential contamination. Alternatively, if such systems are established, the tool 12 can make use of such systems to fine tune its internal metrics for modeling food events and to triangulate against available food tracking information to determine likely sources of illness.

A user interface 34 is provided to allow one or more authorized users to access the tool 12 in order to model various events and/or to strategize as to how to respond to an evolving event. The user interface 34 may be a standalone program, a client run-time, a web interface, or any other user friendly interface. In a preferred embodiment, the interface 34 is a web-based user interface, which allows an authorized user to access the system 10 using any security enabled web browser, either over an internal network, a wireless network, or the Internet.

In general, each database 14A, 14B, 14C and 14D stores vectors of information. As previously mentioned, each database may be multidimensional, meaning that a data fact is viewed as a mapping from a point in a space of dimensions into one or more spaces of measures. For example, within the food distribution profiles database, there are a number of different kinds of measures, such as number of heads of lettuce harvested, number of heads of lettuce sold, number of heads of lettuce consumed, and the like. Each of these can be analyzed in terms of dimensions. Number of heads of lettuce sold, for example, can be analyzed in terms of customer type, distributor, volume per sale, date of sale, geographic region, and the like. Dimensions can be further organized into hierarchical levels, such that the geographic region might be part of a larger region, and so on.

Figure 3:
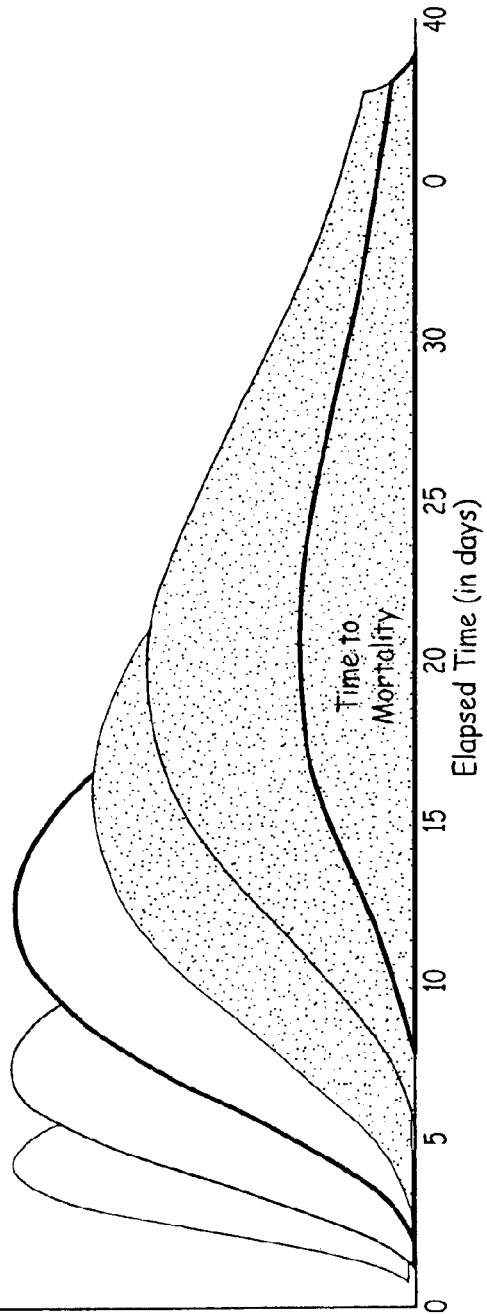
FIG. 3 is a graphical representation of a food incident profile according to the present invention

Data for the food distribution profiles database 14A is derived by tracking food from harvest to consumption for each specific food product over a period of years. As shown in FIG. 3, the compiled data can be illustrated as a series of layered graphs.

Generally, the Food Incident Profiles 12 represent a day-by-day statistical analysis of the quantity of product at each identified stage of the distribution chain for each product. In other words, lettuce, strawberries, corn, and potatoes each have their own distribution profiles. Depending on the particular product and the statistical variance in the distribution data for each product, the profile for any particular product may be relatively static over long periods of time or may vary with the season. Each product can be handled differently.

A food distribution profile can be developed for each fresh produce item. Then, the distribution profile can be coupled with profiles for various harmful pollutants and naturally occurring pathogens to form a food incident profile. In general, the food distribution profile is produced for any food item by collecting and cataloging distribution data for the food item over a period of time. The system was developed for fresh produce, but can be applied to virtually any food product and any contamination agent.

In general, the food distribution profiles illustrate how broadly fresh produce items are distributed across the country and the velocity at which the selected items move through the distribution system. However, the profiles are utilized by the APMT 12 to model the extent of consumer exposure to a food incident, to locate product within the distribution chain, to identify where to direct containment efforts, and to determine the likely efficacy of available intervention measures.

Generally, each profile is created by tracking the movement of a specific product temporally and geographically through each link in the distribution chain. Over time, the profiles become increasingly accurate and may be used to track product distribution.

As shown in FIG. 3, the food distribution profile information and the Agent/contaminant profile information can be combined to provide a graphical illustration of the progress of contaminated food product from harvest to mortality. In particular, the y-axis of the graph represents a statistical distribution of the percentage of product and/or percentage of infected consumers. The y-axis intersects the x-axis of the graph at day zero (0), which represents the day the food product is harvested, in the case of fresh produce for example. At day 1, the harvested and contaminated food product begins to arrive at retail locations. The contaminated food product (in this instance) typically arrives at the retail outlets within a day or two of harvest, and may remain on the shelves at the retail location for 1 to 10 days.

Once the contaminated item reaches retail shelves, it begins to be sold and taken to consumer's homes. Beginning at 1 and a half days (1.5 days), consumers begin purchasing the food product and taking it home. Typically, consumers can store such produce from half a day to a week or so before consuming the product. As shown, the time at the consumer's home may be half a day to six days (1.5 to 16 days from the day the food product was harvested). The profile shows that the food was consumed between half a day and 10 days after purchase (meaning 2 days to 26 days after harvest).

After the food is consumed, it may take several days for symptoms to begin to appear. After symptoms appear, it may take several more days for a consumer to seek medical attention. In extreme circumstances, consumers may die from contaminated food, and it can be several days after seeking medical attention before the consumer dies (7 days to 39 days after harvest).

In general, the food profiles are based on product-specific information. For Lettuce for example, the time from harvest to processing at the distribution center is approximately two hours, based on distance evaluations and trucker interviews. Between time in the distribution center and time in shipping, all of the harvested lettuce reaches the stores within about thirty-six hours. Retailers estimate that received products are placed on the shelves within twenty-four hours of receipt, and the products are typically sold within one to three days of its arrival at the store.

At this point, it is estimated that the first onset of symptoms from illness caused by contaminated lettuce would be noticed within forty-eight hours. Since most people do not immediately attribute illness to food items, medical literature suggests that most infected individuals will seek medical attention within an additional seventy-two hours. Identification of the illness and its potential source may take some time, but would probably occur within ninety-six hours, and the decision whether to recall the product would be made at that time.

Generally, the development of each food profile requires a source profile (detailed breakdown of tonnage of production at all geographic locations at various times of the year). The food profile also requires a distribution profile (location and quantities of products at each identified stage of the distribution chain from harvest through purchase), and a consumption profile (product storage and usage by consumers). As previously mentioned, this information is derived from interviewing producers, truckers, and others.

The contaminant/agent profile requires a clinical disease progression profile (pollutant/agent specific disease symptoms, progression and outcomes), and public health response profiles (public health response times—best, most likely, and worst case scenarios). Both the progression profile and the public health profile can be derived from existing public health data.

In many cases, the food profiles 12 depend on several factors in addition to the product type (for example, iced vs. non-iced green onions). These additional factors, termed "discriminants" are identified as a part of the profile development for each food item, and a profile is built for each combination of the selected food type with the other external discriminants that have a significant effect on the profile.

The Profile for a specific food product will vary with changes in some external factors (the "discriminants"). For some products, seasonality will likely be one such discriminant—for example, it seems logical that the profile of lettuce out of Florida would look somewhat different from the profile of lettuce out of Salinas.

It is believed that there will be key discriminants for each food item, but the relative importance of each discriminant will be determined over time as the profile data for each item improves. If changing the value of a discriminant has a significant effect on a profile, then different profiles will be developed for each such value.

While growing seasons (and therefore particular growers) may vary for each food item, it is believed that competitive pressure tends to force a given product at a given time of year to move at "roughly" the same speed through all distribution channels (where "roughly" means within the limits of accuracy of the profiles).

The food incident profile of FIG. 3 can be used to illustrate the rate at which a food contamination incident is expected to evolve for a particular combination of pollutant or harmful agent for each type of food. Each profile begins with a distribution profile of the movement of the food product from the farm through all stages of production and distribution and through consumption. The profile also contains an agent-specific disease progression profile illustrating the rate at which disease symptoms resulting from the consumption of contaminated food items would be expected to be seen in affected populations. Finally, the profile contains public health response profiles illustrating the likely response by the public health system once affected consumers seek medical attention.

Figure 4:
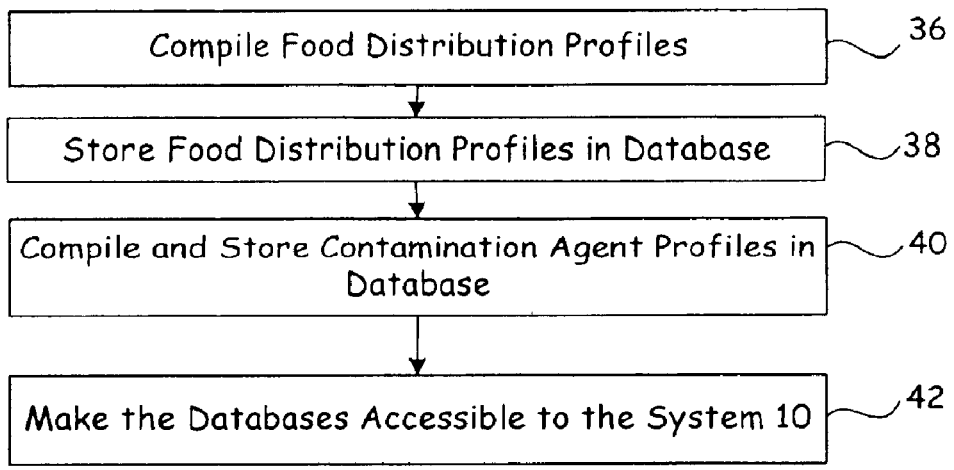
FIG. 4 is a flow diagram of the set up process of the present invention.

As shown in FIG. 4, set up for the system 10 requires compilation of food distribution information and contamination profile information. As shown, the set up requires that the system operator compile food distribution profiles (step 36). Then, the system operator stores the food distribution profiles in a database (step 38). The system operator compiles and stores contaminant/agent profile information in a contaminant database (step 40). Finally, the system operator makes the databases accessible to the system 10 (step 42) for use in analytical and predictive modeling processes.

While the general process is disclosed as being system operator driven, compilation and storage of the food and pathogen profiles can be automated. Alternatively, the data entry and storage can be performed by a third party, and the databases can be made accessible to the system 10.

Figure 5:
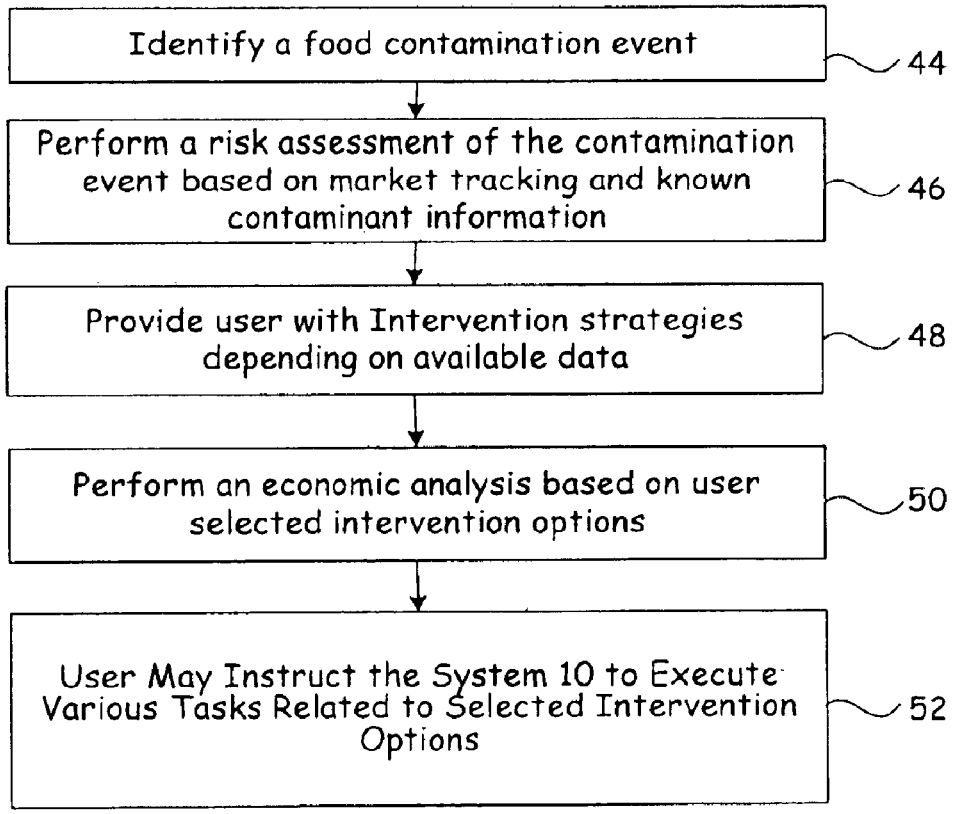
FIG. 5 is a flow diagram of the basic operation of the system of the present invention during analysis of a food contamination incident.

FIG. 5 is a flow diagram of the operation of an embodiment of the system 10. The user identifies a food contamination event (step 44) and selects various parameters. The system 10 then performs a risk assessment of the contamination event based on market tracking and selected (or known) contaminant information (step 46). As the risk assessment progresses, if the user chooses to intervene in the food contamination event, the system 10 provides the user with intervention options depending on the available data (step 48). If the user selects an intervention option, the system performs an economic analysis based on a chosen intervention strategy (step 50). Finally, the user can instruct the system 10 to act on a selected intervention strategy (to intervene) in the contamination event based on the available information, the associated risk assessment and the economic analysis (step 52). Specifically, the system 10 may be configured to initiate selected interventions, such as notifying news outlets, initiating a recall, and the like.

Figure 6:
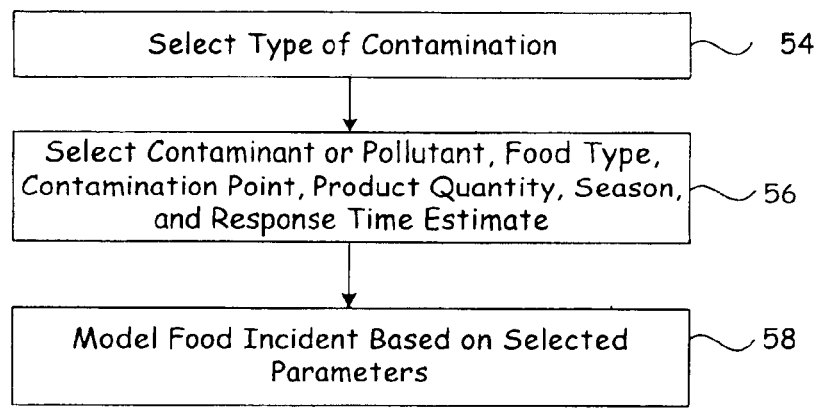
FIG. 6 is a flow diagram of a user interaction for setting up a food incident model.

FIG. 6 is a flow diagram of an embodiment of the user interface. First, the system 10 presents the user with a window for selecting a type of contaminant. The user selects type of contamination (step 54). Then, the system 10 presents the user with a window for selecting the particular contaminant or pollutant, the food type, the contamination point, the product quantity, the season and the estimated response time. The user selects the contaminant, food type, contamination point, product quantity, season, and response time estimate (step 56). Finally, the user initiates the modeling process, and the system 10 models the food incident based on the user-selected parameters (step 58).

Figure 7:
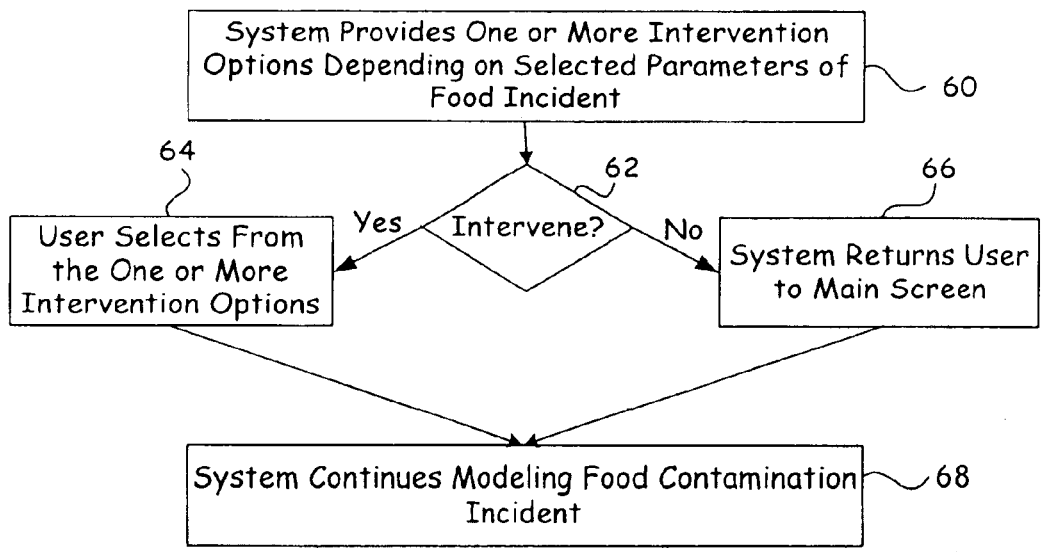
FIG. 7 is a flow diagram of a user interaction with the intervention component of the present invention.

FIG. 7 is a flow diagram of an embodiment of the operation of the system 10 with respect to intervention options. Once the APMT 12 begins modeling a food incident, the user can choose to view available intervention options, based on information related to the food event. When the user chooses to view intervention options (such as by clicking a button within the APMT 12 software, the system 10 provides one or more intervention options depending on the user-selected parameters (step 60). If the user chooses to intervene (step 62), the user selects from the one or more available intervention options (step 64), and when the user is finished, the system continues modeling the food contamination incident (step 68) based on the selected intervention option(s). Alternatively, if the user chooses not to intervene (step 62), the system returns the user to the main user interface (step 66) and continues modeling the food contamination incident (step 68).

In general, the intervention options provided to the user (step 60) may vary, depending on what is known about the particular food incident. For example, if the food source of the illness is unknown, intervention options are limited, as will be discussed later with respect to a software implementation of the invention.

As shown in FIG. 8, upon launching the APMT 12, the system 10 runs various internal software processes, and provides the user with an interface or window 70 requiring the user to select between an unintentional contamination or an unintentional contamination event (shown as mouse clickable buttons 72). Unintentional contamination includes such things as exposure of fresh produce to a naturally occurring microorganisms or bacteria, failures in pasteurization or storage that allow naturally occurring microorganisms to reconstitute, and the like. By contrast, intentional contamination involves an actor who chooses to contaminate a food product or item at some point in the food distribution chain, with natural contaminants or artificial agents (such as when someone tampered with Tylenol brand of acetaminophen capsules in 1982).

FIG. 9 shows the window 70 the APMT 12 software application after the user has selected an unintentional contamination. In addition to maintaining the incident type buttons 72, the APMT 12 software application provides the user with various criteria from which to choose (shown as pulldown or drop down lists 74) and a run button 76 for initiating the modeling process. Depending on whether the user selected intentional or unintentional contamination, the options within each pulldown menu and the criteria may vary.

As shown, the tool 12 allows the user to select a contaminant from a drop down list 74A. The contaminant drop down list 74A may include any number of possible contaminants, each corresponding to a contaminant profile stored in a database. The contaminants may include C. Botulinum Toxin, Salmonella, E. Coli, and the like.

The tool 12 also allows the user to select the food product from a food drop down list 74B. Selection of Milk, for example, may change the contents of the contaminants list 74A, in part, because various microbial and other contaminants may be relevant only to specific food products. Similarly, the contamination point (drop down list 74C) and contaminated product quantity (drop down list 74D) criteria are also context specific. For example, if the food item selected from the food list 74B is lettuce, the contamination point list 74C includes the field, distribution center, and the like, whereas a food selection of "Milk" causes the contamination point list 74C to include the dairy, milk processors, shippers, and the like. Thus, the drop down lists 74 are context sensitive and tied directly to the food distribution data stored in the food distribution profiles for each food item.

The final two modeling criteria in the drop down lists 74 are based on the recognition that product distribution profiles may vary according to the particular season (drop down list 74E), and that public health response times (drop down list 74F) vary by region and by type of incident. Specifically, this parameter appears only for foods that have seasonal variations. For example, certain food products are seasonal to the extent that they may originate from different areas at different times of the year. Thus, the food distribution profile may change over time, such as by seasons or month to month. The season drop down list 74E for "Season" includes "Spring", "Summer", "Fall", and "Winter" as selection options, as well as each month, so that the level of granularity can be adjusted for each model.

The public health response time drop down list 74F is a guess or estimate of the time it might take public health authorities to detect a food related illness. Specifically, this parameter refers to the time between report of an illness and identification of the outbreak. In some areas of the country, such as in Minnesota where significant government resources are directed to public health, the response time might be in days, whereas in other, more rural areas, the response time can be longer. Thus, the public health response time criteria allows the user to select between "Normal Response", "Rapid Response", and "Slow Response", or alternatively to select a number of days. Alternatively, the public health response time can be modeled, based on public health records.

The drop down lists 74 provide various criteria allowing the user to customize the model to fit fact scenarios according to available information. More importantly, the drop down lists 74 allow the user to select criteria in order to construct models based on variations in season, in responsiveness, in contaminant type, and so on, allowing the tool 12 to provide statistically relevant information over a wide range of possibilities.

FIG. 10 shows a window 70 corresponding to a user selection of an intentional contamination event. The scenario indicated is "Intentional". As shown, the criteria (shown as drop down lists 74) are largely the same for user selection purposes. However, instead of selecting a contaminant (drop down list 74A), the user selects an "agent" from the list. In this instance, since the contamination event is intentional, the list of agents includes chemical and some cultivated microbial agents that might not appear in the "unintentional list". For example, unintentional contamination of milk with arsenic is unlikely, so arsenic is not listed as a possible "unintentional" contaminant, but could be listed as a possible "agent".

In general, the tool 12 prompts the user to make relevant choices from a group of available criteria. Values available from the various criteria are interdependent, such that the lists may adjust according to user selections so that only valid selections are possible, based on the food item.

Some examples of food items that are modeled include head lettuce, chopped lettuce (such as for food services), bagged lettuce, dry cheese, ground beef, green onions, milk, potatoes, and the like. Some possible selection values for agents/contaminant, independent of any particular food item, include such microbial pollutants as C. Botulinum Toxin, Cholera, Salmonella, E.Coli, Shigella, Typhoid, Gastro Intestinal Anthrax, and the like, and include such chemical pollutants as Sarin, Somain, Tabun, VX and the like. Additionally, radiological contaminants are also included.

As previously discussed, available options for the "Contamination Point" criteria are food type specific. During assembly and compilation of the food profiles, the stages of the food distribution chain for each food item are identified. For lettuce, for example, the stages in the distribution chain include the following: field, truck to hydrocooler, hydrocooler, truck to distribution center, distribution center, truck to retail stores, and retail store. For milk, beef, or other food items, the stages are different. Milk, for example, includes pasteurization and bottling stages.

The contaminated food product quantity is also context specific. For example, if the contaminated product is milk and the contamination point is the dairy farm, the contaminated product quantity might be in terms of liters or gallons, as opposed to number of cartons, whereas if the contamination takes place after bottling, the quantity would be in number of cartons. For lettuce, the quantity would be in number of heads, unless the food type is bagged lettuce, in which case the quantity would be in number of bags, and so on. Thus, the contaminated product quantity is a pull-down menu with values that vary according to the selected food type and contamination point.

Once the user is finished selecting the desired criteria, the user clicks the "Run" button 76, and the tool 12 begins modeling the food incident according to the selected parameters and according to compiled food distribution and contaminant profiles.

FIGS. 11–31 illustrate the model display window 78 for an embodiment of the system 10 of the present invention, which in this embodiment displays automatically upon completion of the criteria selection. The display window 78 contains information generated by the tool 12, modeling a specific food incident. As shown, the selected criteria (selected from the drop down lists 74) for the food incident are displayed across the top of the window (indicated by reference numeral 80). In this instance, the modeled food contamination incident involves an unintentional food contamination incident effecting 240,000 heads of Head lettuce. The agent/contaminant is *salmonella*, which was introduced to the head lettuce at the field. The food incident is being modeled for the summer, and the public health response time is selected to be rapid.

Generally, the tool 12 provides access to a large amount of information. As shown, below the user-selected criteria, the tool 12 provides a row of tabs 82: "Incident Profile" tab 82A, "Food Sourcing Profile" tab 82B, "Consumption Profile" tab 82C, "Agent/Contaminant Profile" tab 82D, and "Morbidity/Mortality Profile" tab 82E. Additionally, just above the row, the tool 12 provides the user with a "Change Input" button 84 for altering the criteria for the model. The "Change Input" button 84 allow the user to change the model at any time, either as new information comes available, to correct an error, or just to see how different fact patterns alter the model.

Figure 11:
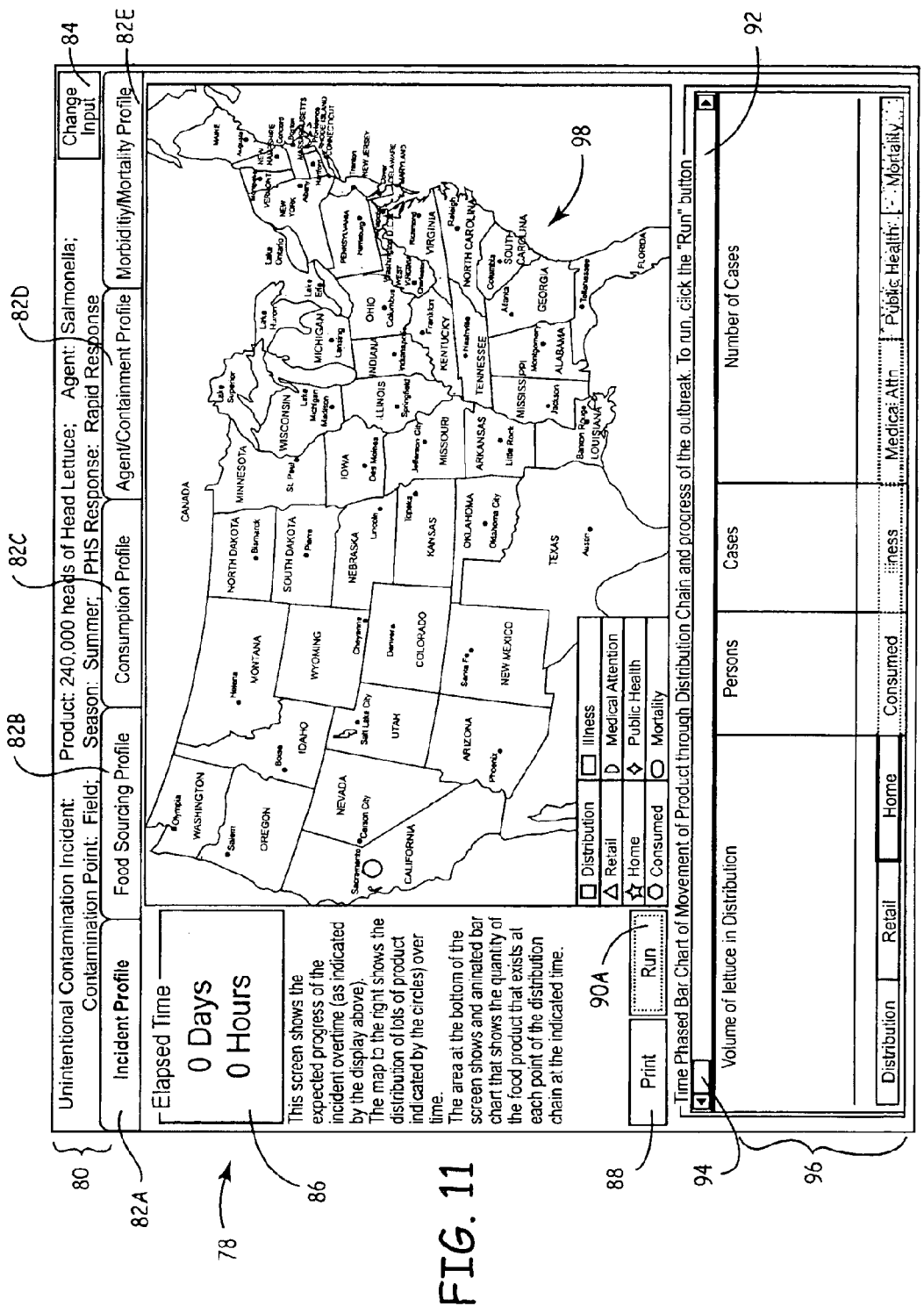

In FIG. 11, the tool 12 is showing the incident profile window, which is accessible via the "incident profile" tab 82A. The incident profile window displays product distribution profile and contaminant profile information graphically and provides easy access to additional information and to intervention options.

In general, the incident profile window shows the expected progress of the selected food incident over time, as indicated by the time display 86. The elapsed time at this frame is zero days and zero hours, meaning that the simulation has not started. Generally, the time is to evaluate statistically the progress of the food product through the distribution chain, all the way to consumption. The time element is also used as a factor for the contamination profile. In this instance, since the product selected is lettuce, the time is calculated from the time of harvest.

At any point during the modeling process, the user can click the print button 88 to print the current screen. Additionally, the "Run" button 90A becomes a "pause" button 90B when the modeling process is in progress, so that the user can study a particular time frame within the model.

As shown, a bar 92 extends horizontally across the window, illustrating the progress of the particular model. The user can advance or back up the software by clicking and dragging the progress marker 94 on the bar 92. Finally, the bottom portion of the window shows a time phased bar chart 96 of the movement of product through distribution, as well as the progress of the resulting outbreak. As shown, with zero days and hours elapsed, no product has been distributed.

Finally, the window provides an animated map 98 of the continental United States. The circle on the map is highlighting the production fields for lettuce. Within the food industry, particularly in fresh foods, there are typically only a handful of locations that supply the majority of produce for the entire country; however, the map will vary depending on the food product of interest. For example, for fluid milk, the animated map 98 is designed to reflect regional distribution. Depending on the specific implementation of the software and on the selected food product, the harvest location may vary and may include more than one producer.

Figure 12:
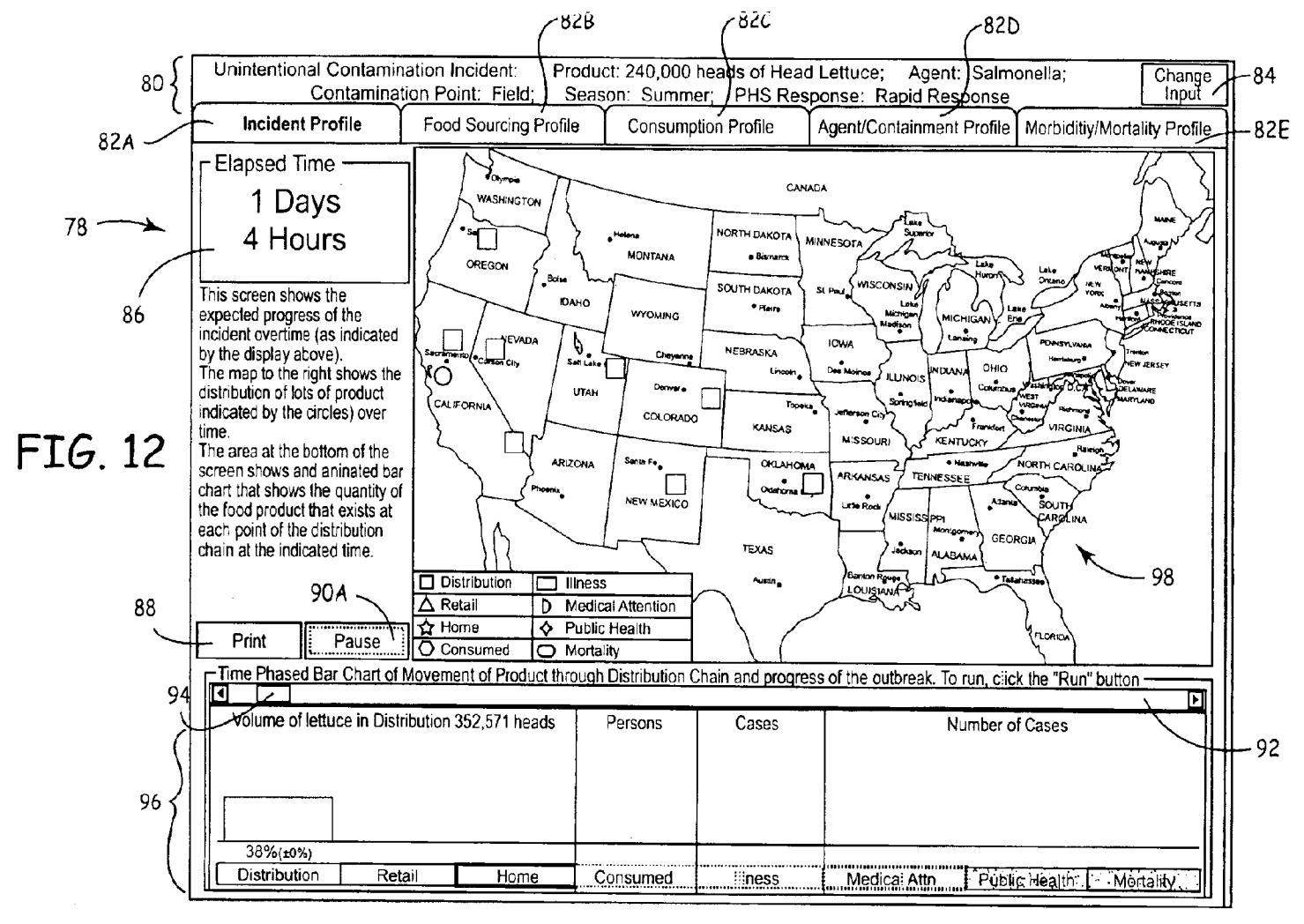

FIG. 12 illustrates the same incident profile window with the same incident parameters after one day and four hours have elapsed (within the software). It will be understood that the elapsed time is time passing in the model (or reference frame), as opposed to actual time. As shown, the map displays the expected locations of the product as it moves from the field through the distribution chain. At this stage, the product has reached distribution centers (as indicated by the squares).

The time phase bar graph 96 portion along the bottom of the window 78 shows that 38% of the harvested food product has reached the distribution center. The food product has not yet reached the retail stores. As the food product moves through the distribution chain, the markers change colors or shapes or otherwise indicate a change to show the most recent stage of distribution at the particular location.

In actual practice, the dots may be color coded to indicate a particular stage in the distribution chain, and the time phase bar charts 96 may be color coded to match. However, as shown herein, the markers have been changed to various shapes for ease of reproduction.

Figure 13:
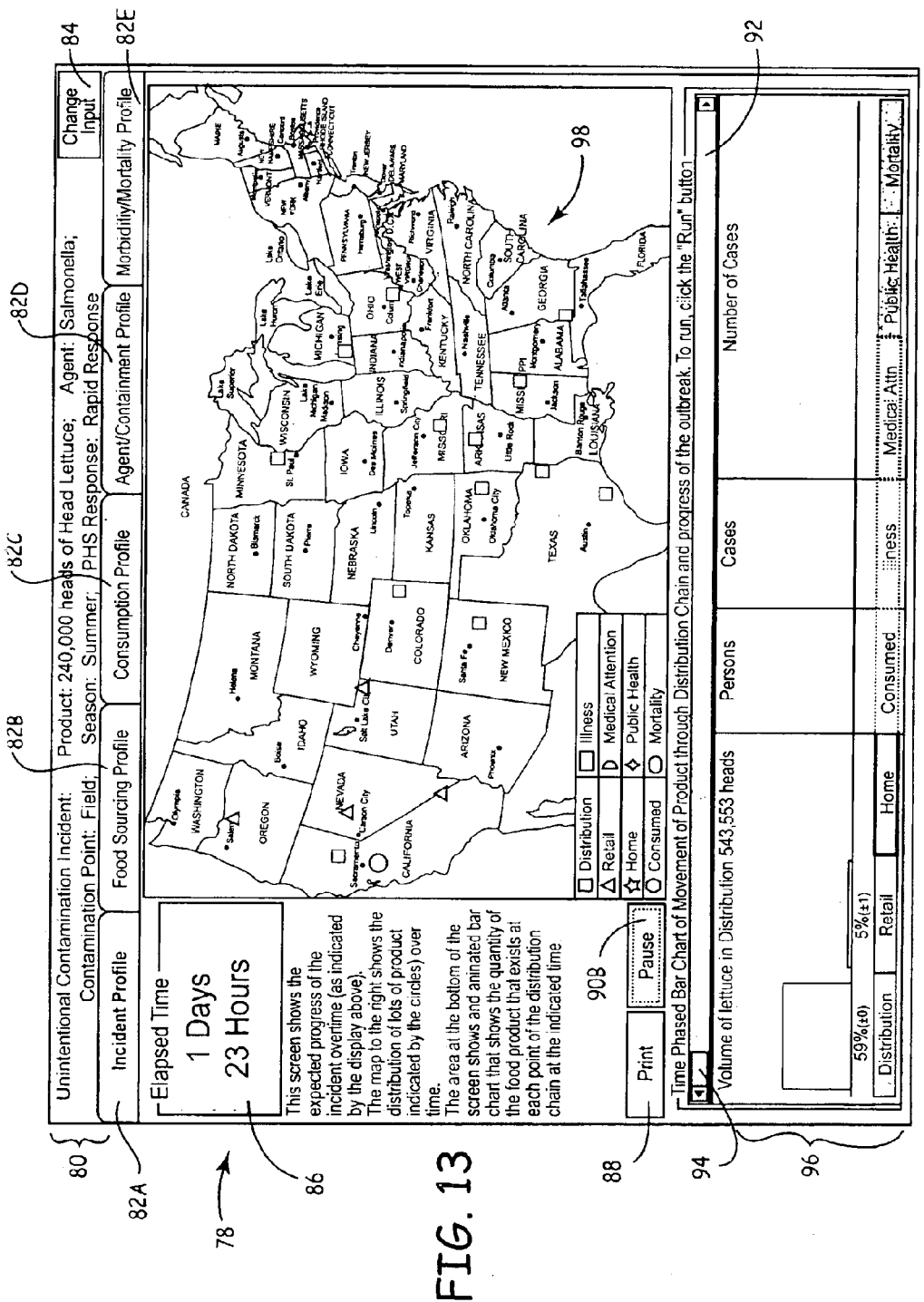

FIG. 13 shows the window 78 at an elapsed time of one day and 23 hours. As shown, five percent of the harvested product has reached retail stores (indicated with a white triangle), and fifty-nine percent of harvested product has reached the distribution centers. The product has moved across almost the entire continental United States in less than two days.

Figure 14:
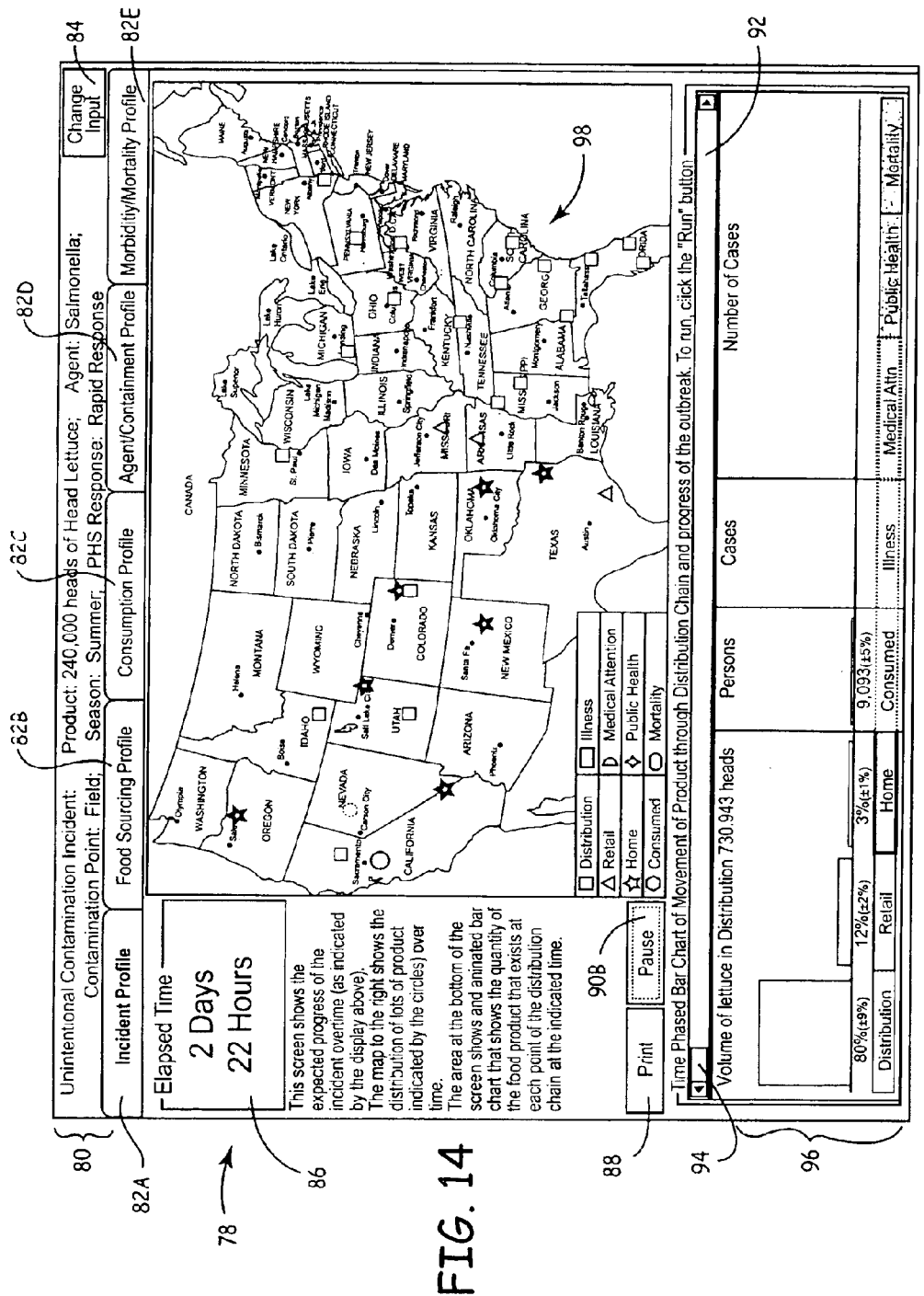

FIG. 14 illustrates the window 78 at an elapsed time of two days and twenty two hours. At this point, eighty percent of harvested product has reached the distribution centers (almost 731,000 heads of lettuce are at the distribution centers), twelve percent is in retail stores, three percent has already been purchased and carried home by consumers, and approximately 9,000 people have already consumed the contaminated product. As can be seen by comparing FIG. 14 with FIGS. 15–29, some of the markers change shape as the food product moves within the distribution chain, and as an outbreak of illness starts.

As previously discussed, the food distribution profile is compiled by interviewing distributors, harvesters and the like, and by monitoring the flow of food through the distribution chain over a period of time. The consumption profile may be built in the same manner by interviewing consumers. Alternatively, the consumption profiles may be independently maintained, and accessed as needed by the tool 12.

Figure 15:
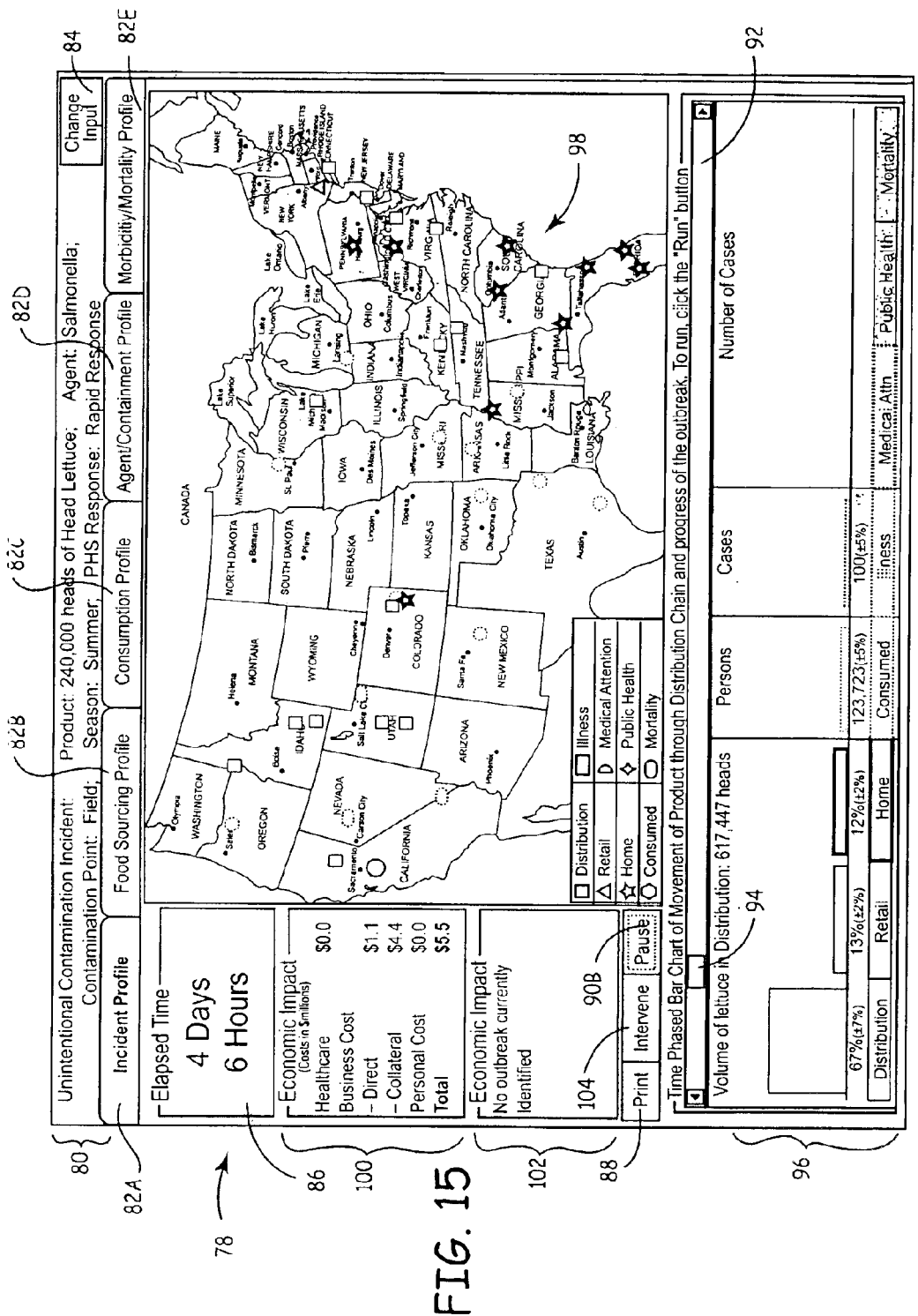

FIG. 15 shows the status of the model at 4 days and six hours. At some time before this screen, a first illness has occurred. The occurrence of illness triggers the economic impact analysis display 100, modeling the financial implications of an unfolding incident.

As shown, the tool 12 predicts that the earliest onset of illness is likely to occur in areas that receive the contaminated food first. As shown, 123,723 households are estimated to have consumed the food item, but only 100 show signs of illness. None have sought medical attention for the symptoms at this point. The households bar graph assumes 2.2 persons per household, and the number reflects household consumption.

Since none have sought medical information, the epidemiological display 102 has no outbreak information. Additionally, the tool 12 provides an additional user option to intervene in the evolving incident by clicking an "Intervene" button 104. The Intervene button 104 will be discussed in greater detail with respect to FIG. 20.

The economic impact analysis display 100 models the costs of an evolving incident, in terms of direct and indirect business costs, healthcare costs, and personal costs, and provides a running total. The economic impact analysis may be based on historical cost data, models of historical costs, or estimates of lost work costs, direct health care costs, and so on.

It is also important to note that the time phase bar graphs 96 across the bottom of the window 78 track the distribution and illness data. Comparing the percentage and volume of lettuce in distribution in FIG. 15 with FIG. 16, the percentage decreases from day 4 to day 6, in part because less product is still at the distribution center. A larger percentage of product has reached the retail locations, has been purchased, and/or has been consumed. Thus, the bar graphs track the bell-shaped distribution of the food distribution profiles.

Figure 16:
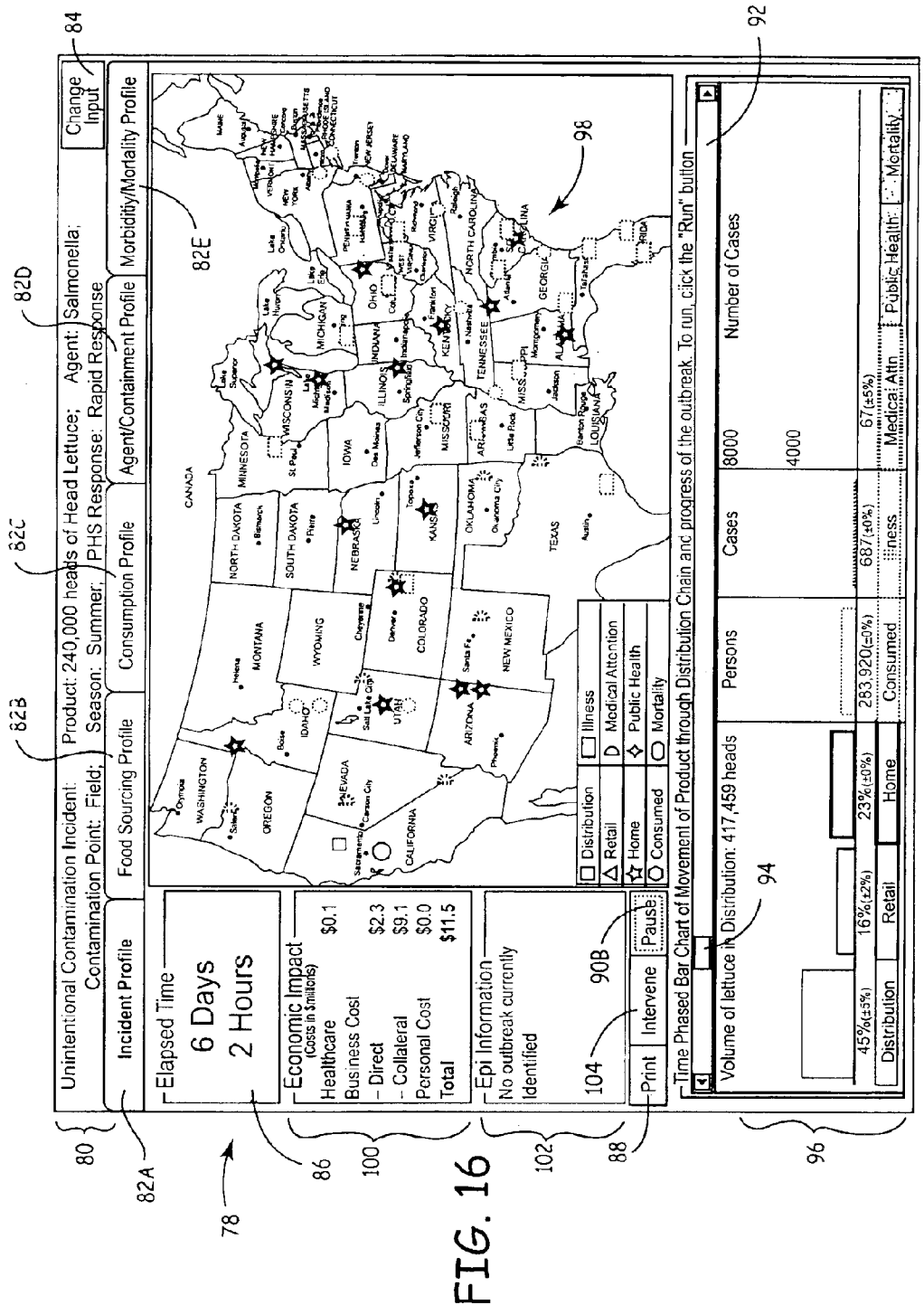

FIG. 16 shows the status of the model at six days and two hours. As shown, more and more consumers are showing signs of illness, and some of the ill people are beginning to seek medical attention (as indicated by the solid triangles). The time phase bar graphs 96 across the bottom of the window 78 shows 687 cases of agent-dependent illness and sixty seven cases of ill consumers seeking medical attention. In particular, the "number of cases" shows the simulated number of illnesses that result from the consumption. This number is based, in part, on the selected quantity of contaminated product, which in this case is 240,000 heads of lettuce.

The economic impact as indicated by the economic display 100 shows that healthcare related costs have reached one hundred thousand dollars (0.1 dollars as indicated in millions). Direct and indirect business costs have risen to $2.3 million and $9.1 million, respectively.

Figure 17:
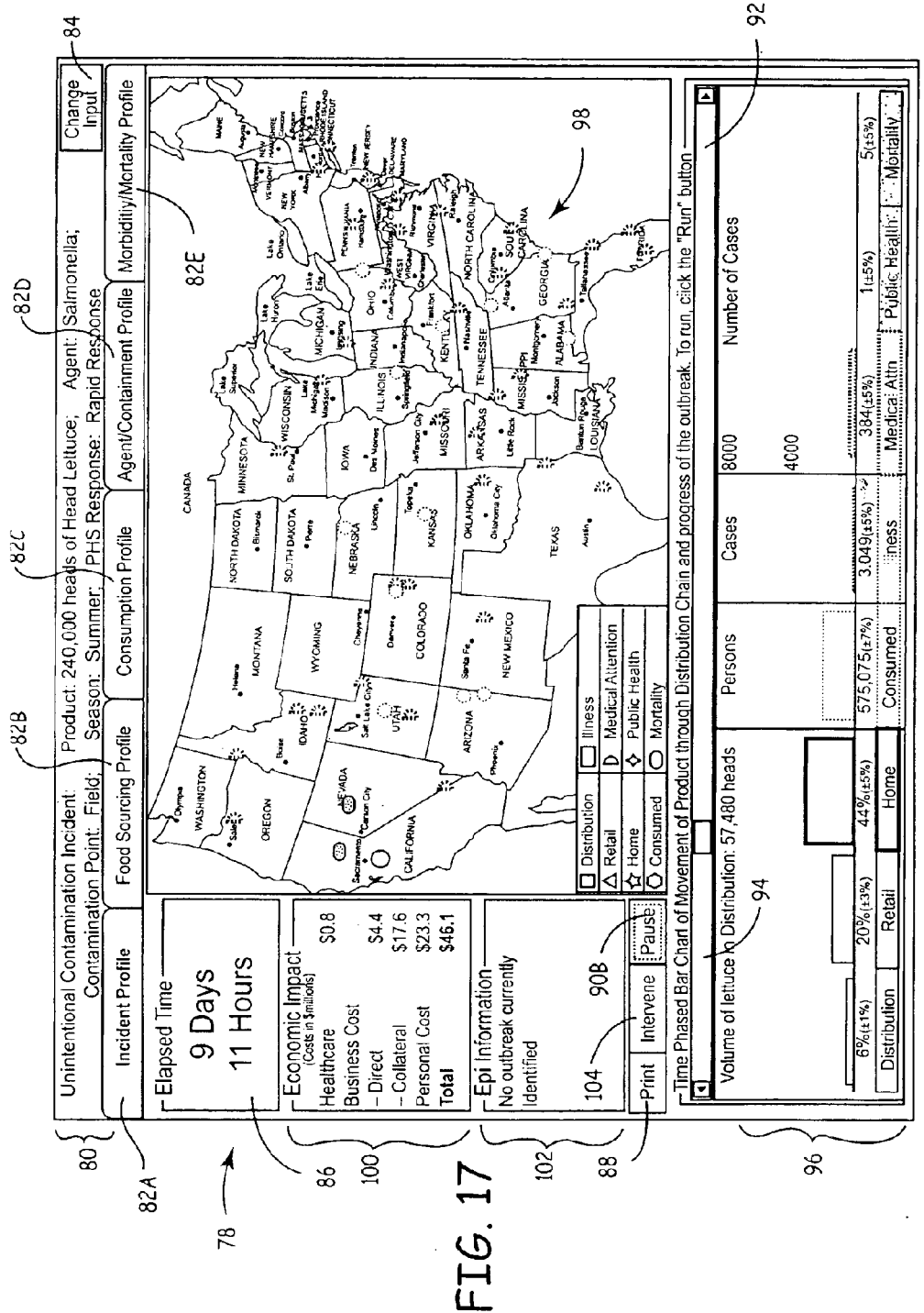

FIG. 17 shows the state of the simulated food incident model at nine days and eleven hours. The time phase bar 96 shows that the number of cases has risen to 3,373, the number seeking medical attention has risen to 429 cases, and only one case has been reported to a public health department or agency. At this point, the total economic impact is estimated to be fifty-one million dollars.

Figure 18:
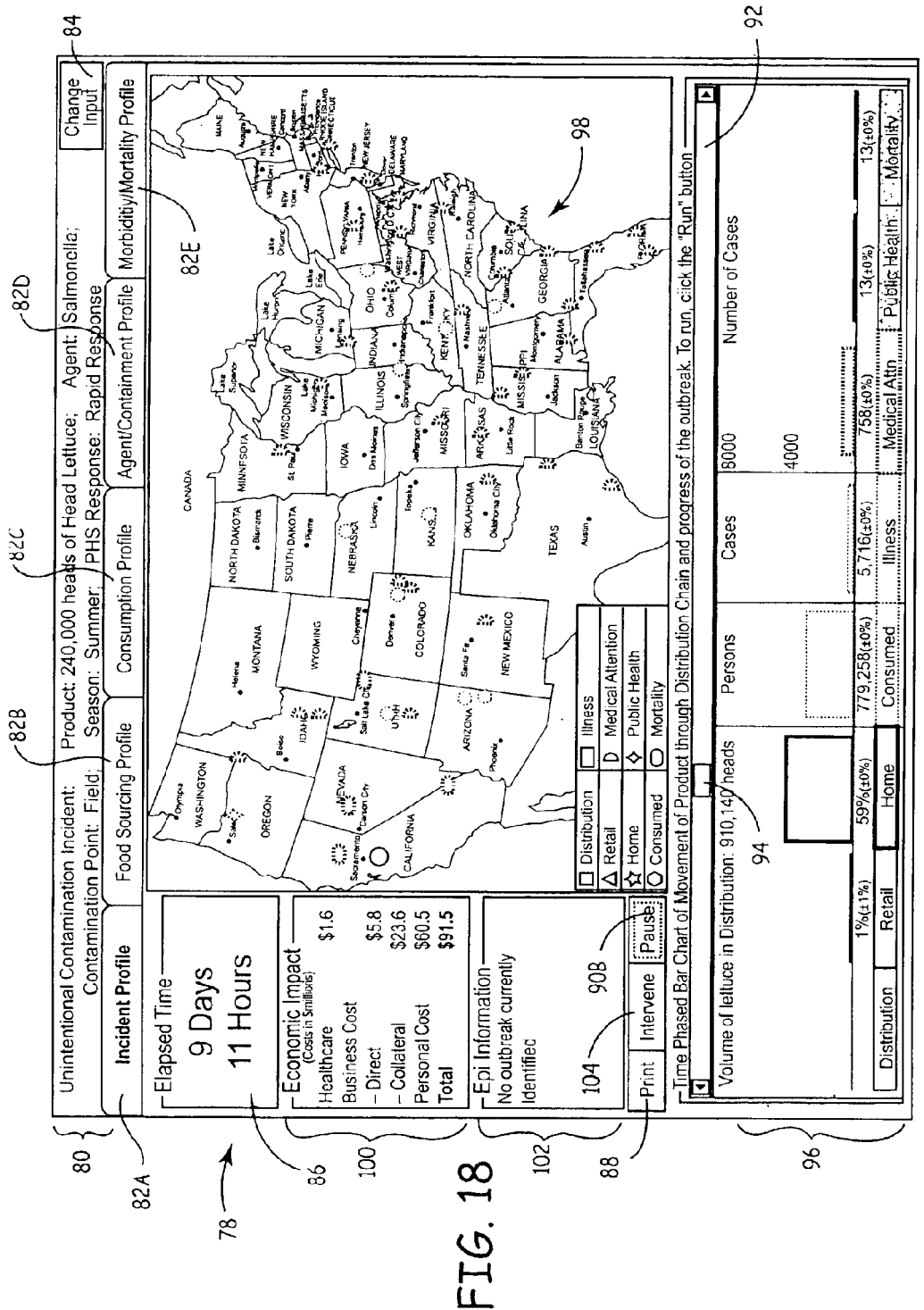

FIG. 18 shows the state of the food incident model at eleven days and twenty hours. At this point, the tool 12 estimates the number of mortalities that would result from the incident. For the ease of depiction, the tool 12 shows all mortalities that are predicted statistically to arise from the outbreak. As before, the economic impact shown in the economic display 100 continues to rise (to over sixty nine million dollars at this stage).

Figure 19:
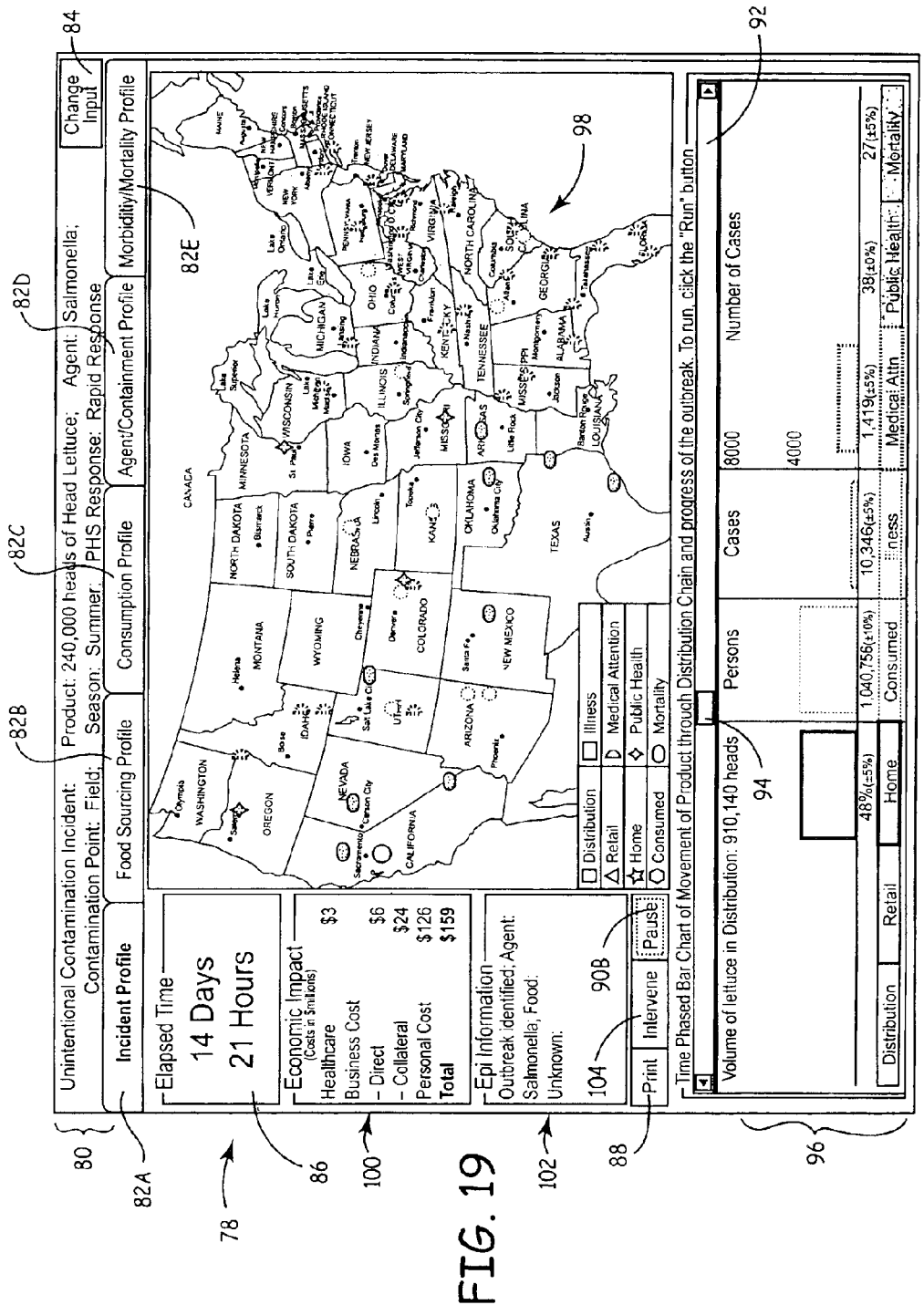

FIG. 19 illustrates the state of the food incident model at day fourteen and hour twenty-one. As shown, the estimated economic impact has reached $159 million, and the number of fatalities estimated has reached 27.

At any point during the modeling process, the user can click the print button 88 and print or export data to spreadsheets or to other systems. Additionally, the model can be posed at any stage by the user, simply by clicking the pause button 90B.

Figure 20:
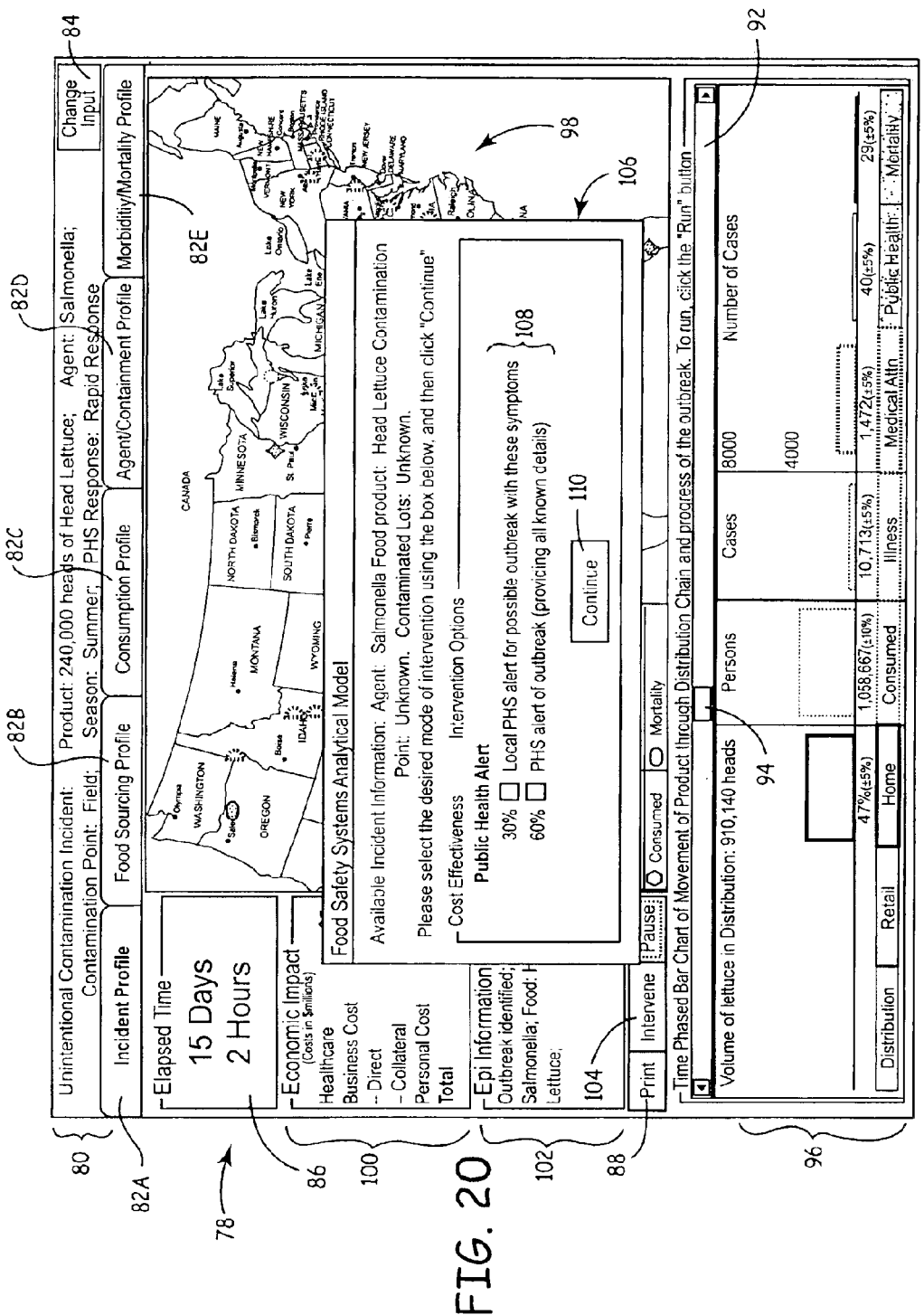

FIG. 20 shows an Intervention window 106, which opens when a user clicks the "Intervene" button 102. Once an event is recognized, possible interventions may be selected to mitigate the incident. As shown, the epidemiological information in the display 102 has been updated to indicate that an outbreak has been identified and that the cause of the outbreak is *salmonella*.

The intervention options 108 shown in the intervention window 106 are based on the available incident information. The model displays feasible interventions in light of the current epidemiological knowledge about the incident. Specifically, alerting public health services (PHS) for possible outbreaks or for particular symptoms is difficult until an outbreak is identified. At this point, given that the food source is unknown, intervening in the food distribution chain is not a permitted option. Clicking the continue button 110 causes the tool 12 to continue with the simulation. Checking an intervention option alters the economic impact and other factors associated with the model. In this instance, no intervention option is selected. However, when a combination of interventions is selected, the tool 12 continues from the current point.

As shown, the only available options are to issue a local PHS alert for possible outbreak with the specific symptoms and/or to alert PHS of the outbreak and providing all symptoms. The estimated cost effectiveness is shown as 30% and 60% respectively.

Specific intervention options will depend on the specific implementation. In particular, a public health agency may have wider resources and different available interventions than a private food distributor. Thus, the options may be customized to fit the specific implementation.

Figure 21:
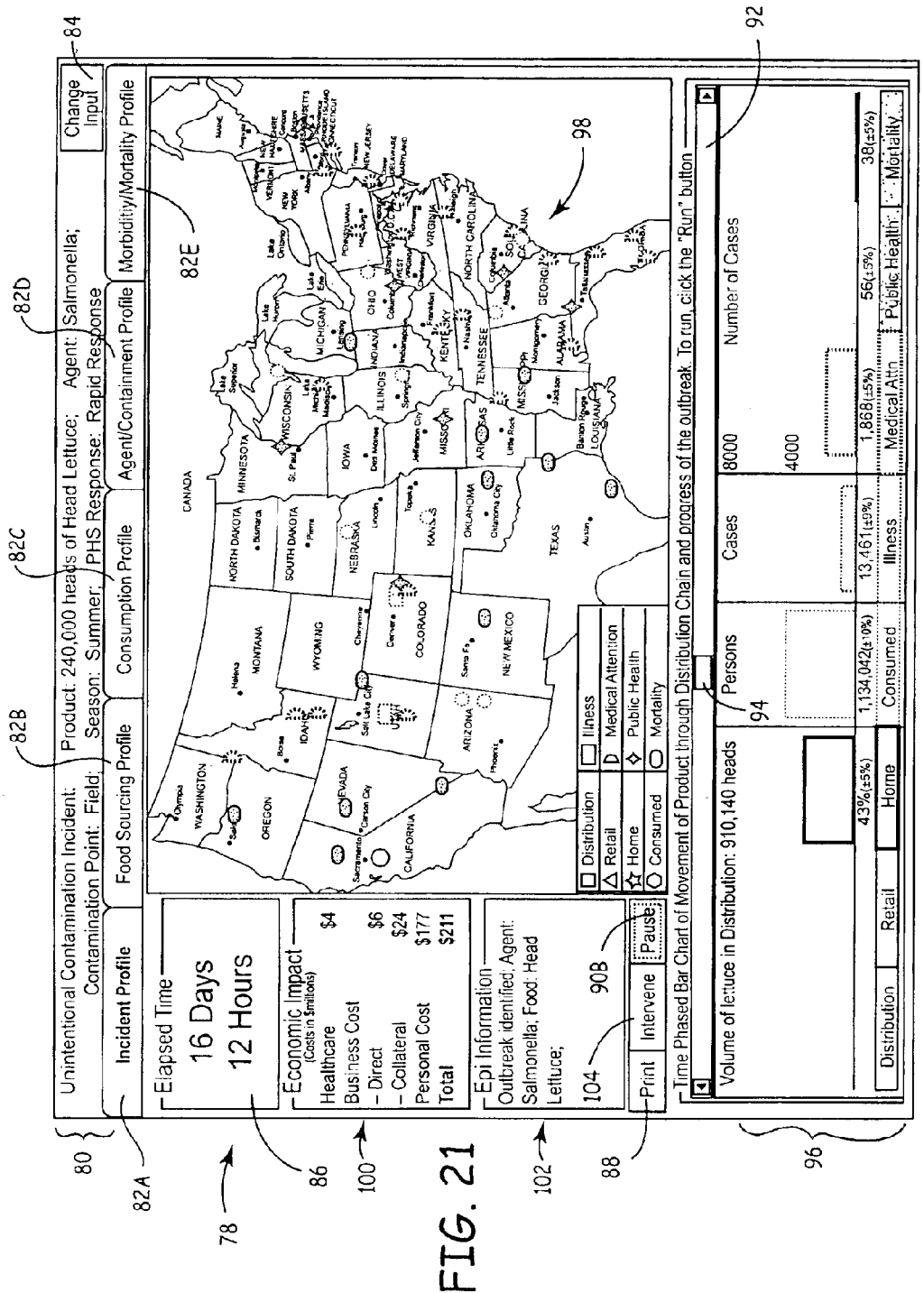

FIG. 21 shows the state of the model at day 16 and 12 hours. At this point, the outbreak, the causative agent, and the food source have all been identified, as shown in the epidemiological display 102. As previously mentioned, the updated information provides a basis for additional intervention options.

Figure 22:
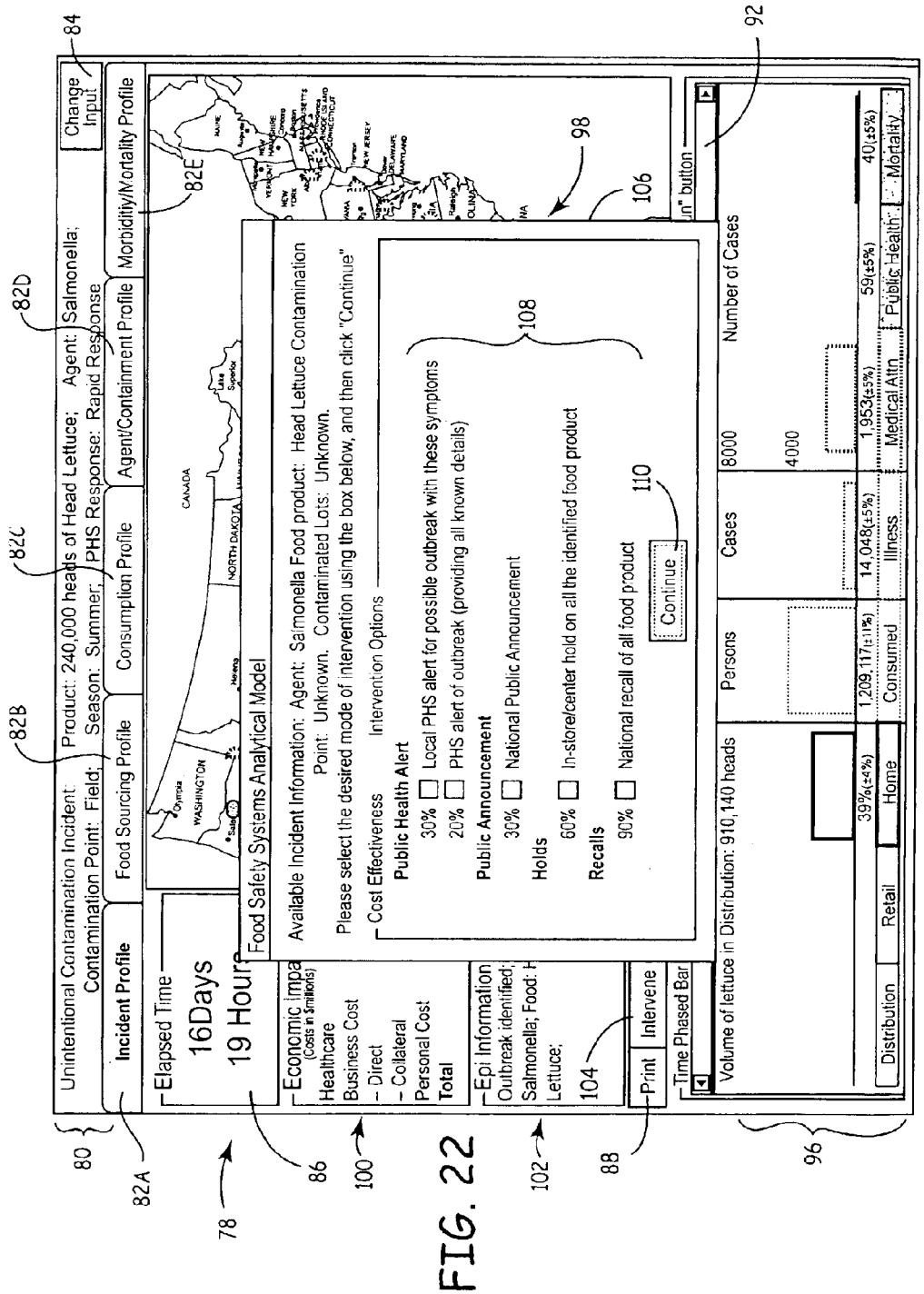

As shown in FIG. 22, clicking the intervention button 104 causes an intervention window 106 to open. The intervention window 106 offers several intervention options 108, including public health alerts, public announcements, product holds, and recall initiatives.

Figure 23:
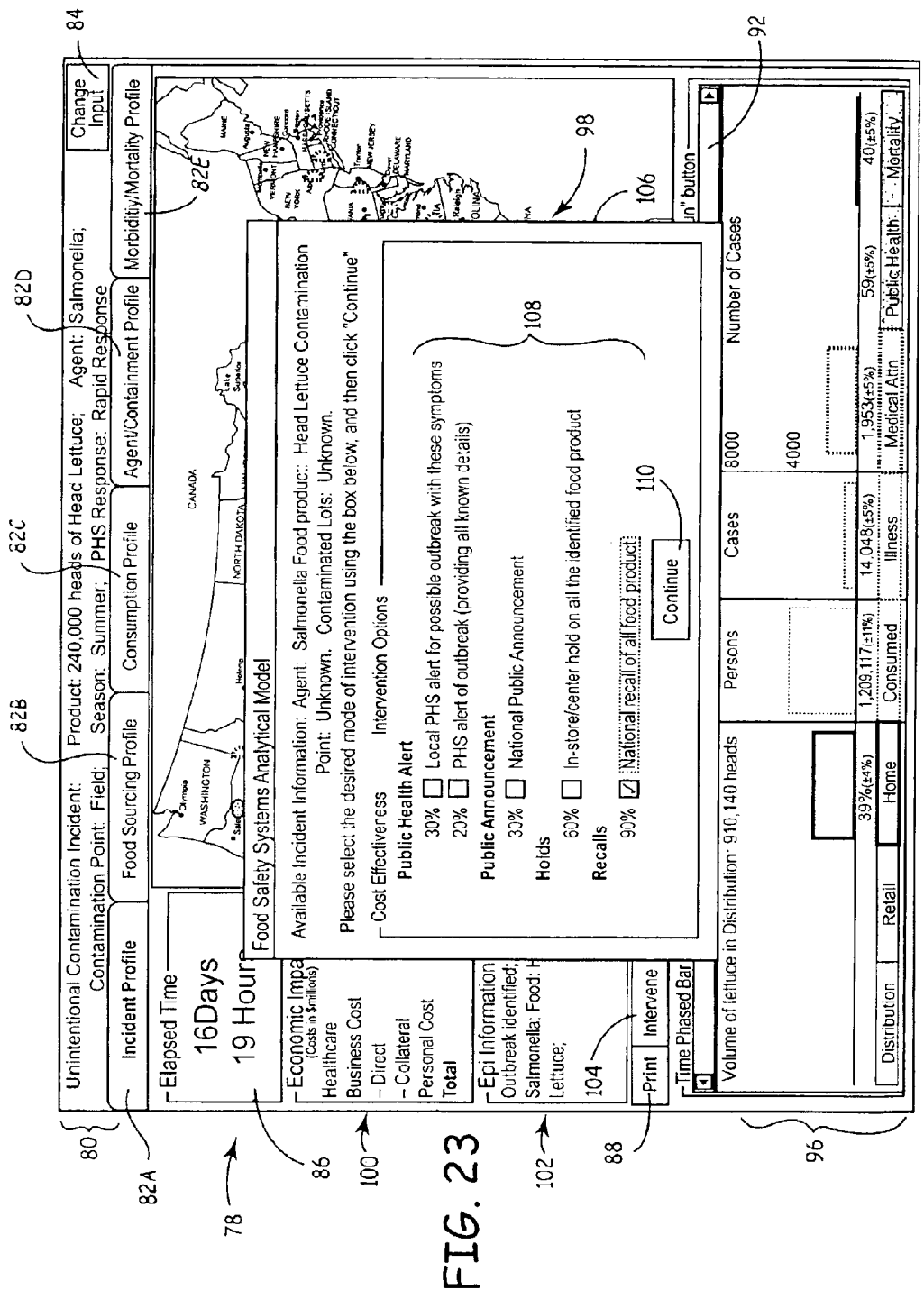

FIG. 23 illustrates the same intervention window 106 with the user selection of "national recall of all food product", which is indicated to be 90% cost effective. By clicking continue, the user alters the model so that the particular intervention impacts the rate of increase in the total economic impact.

Figure 24:
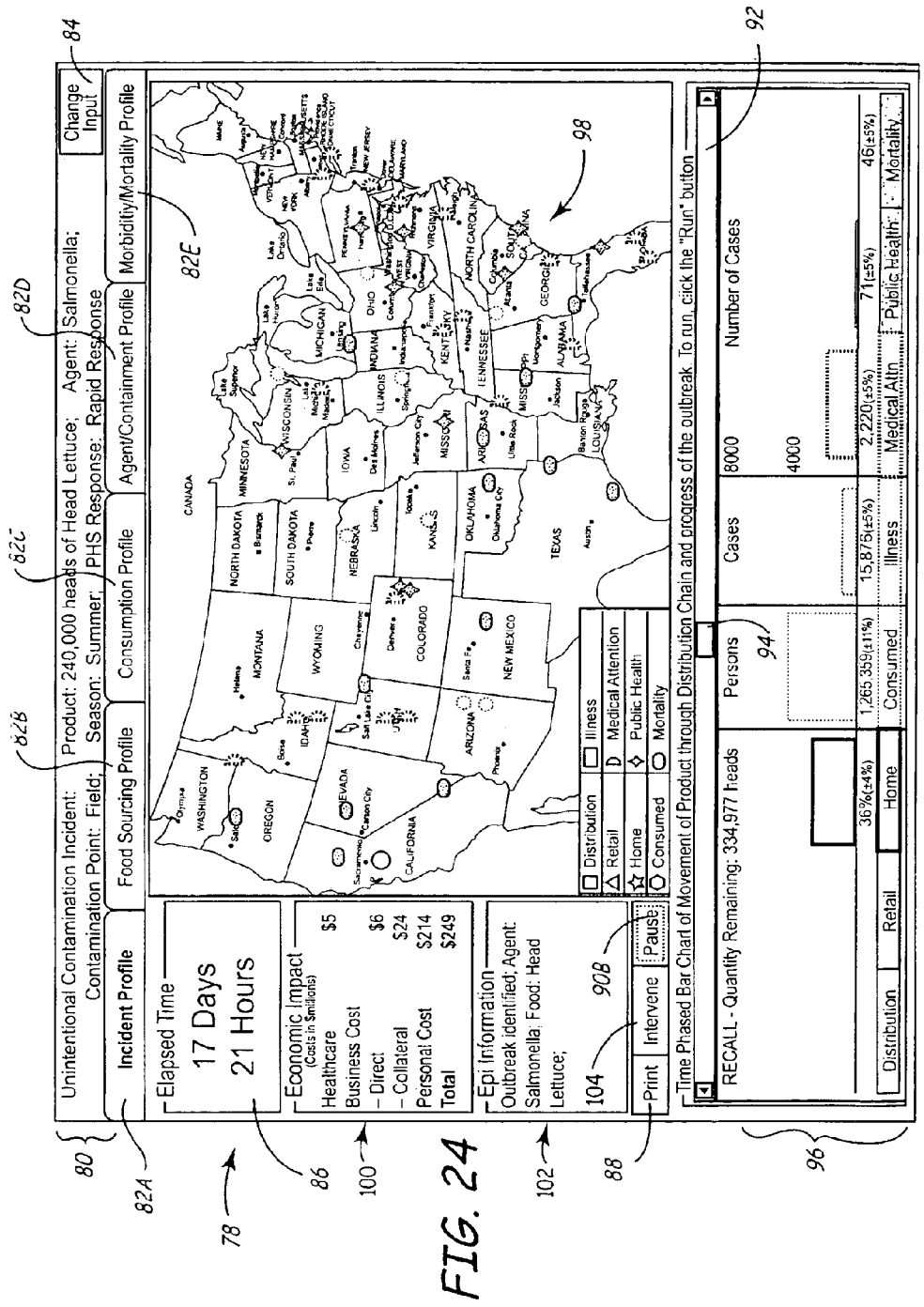
Figure 25A:
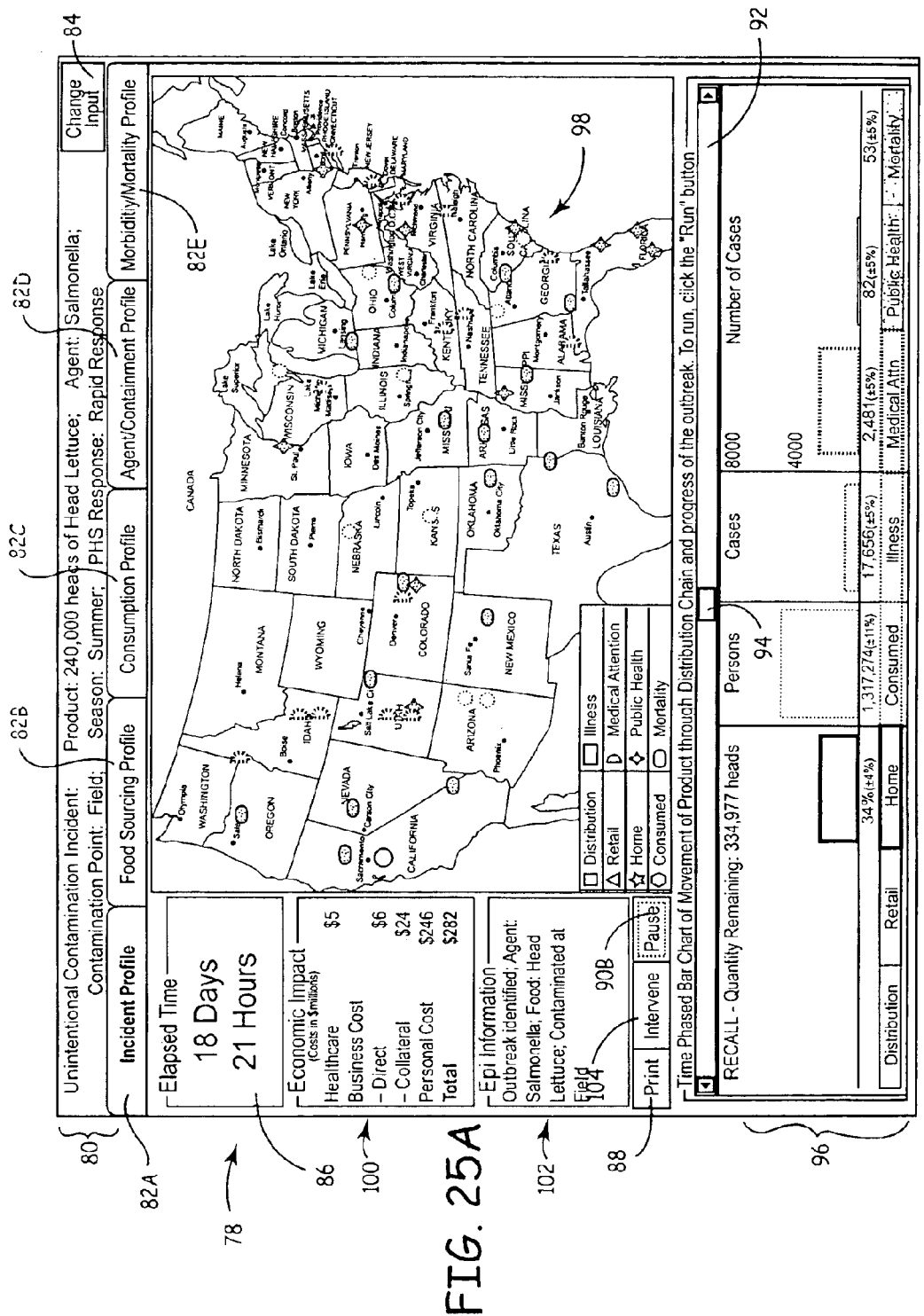
Figure 25B:
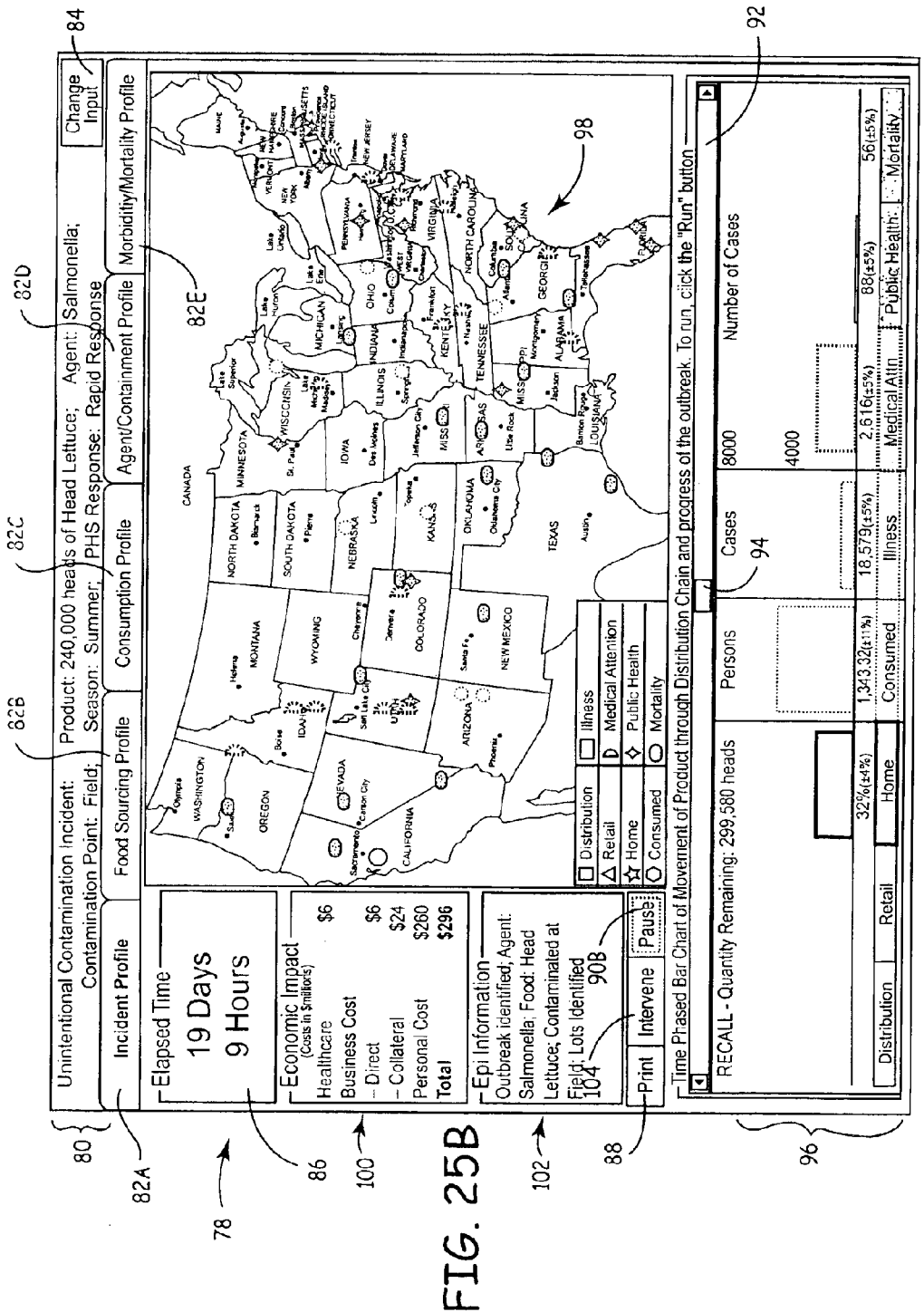
Figure 26:
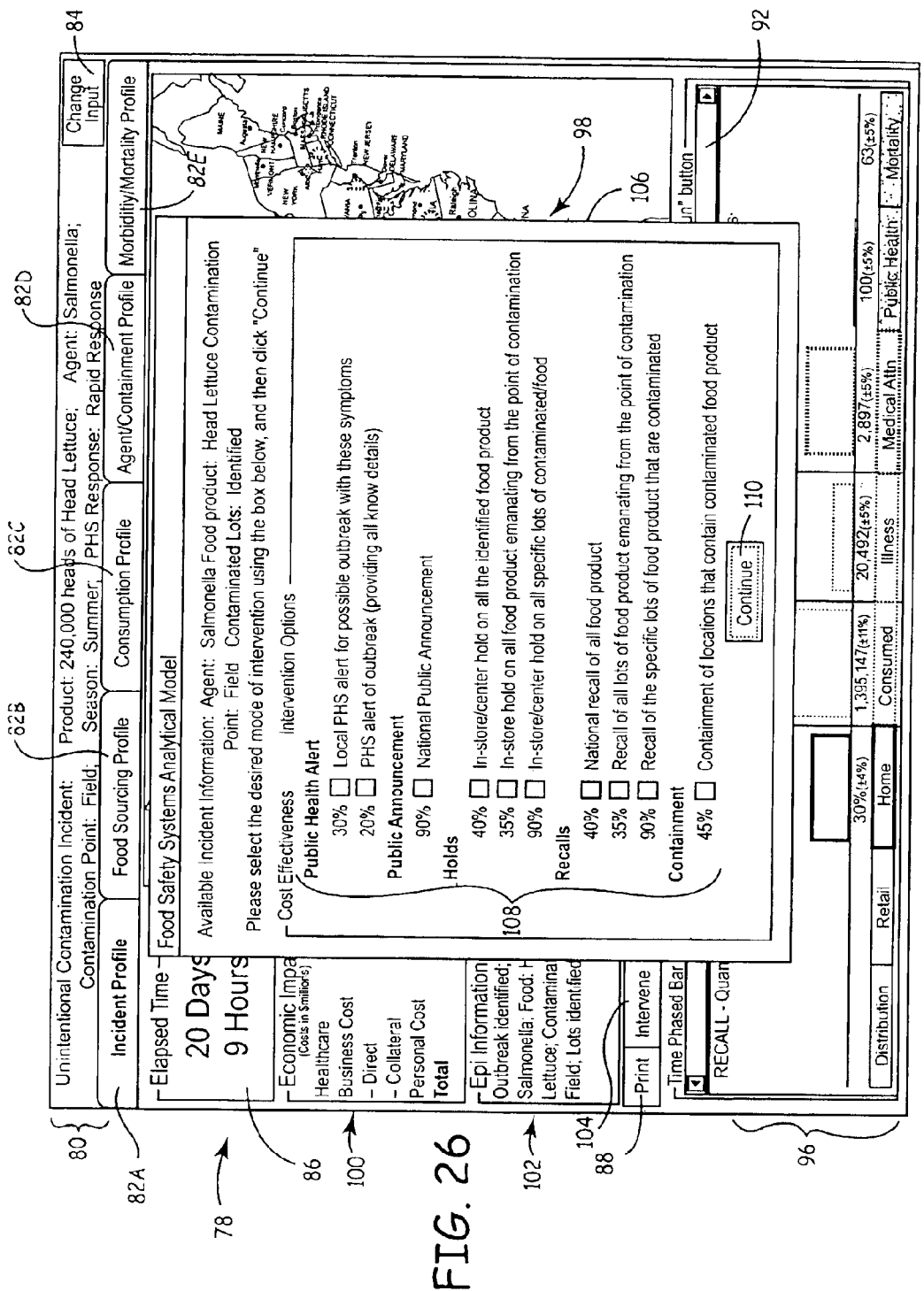
Figure 27:
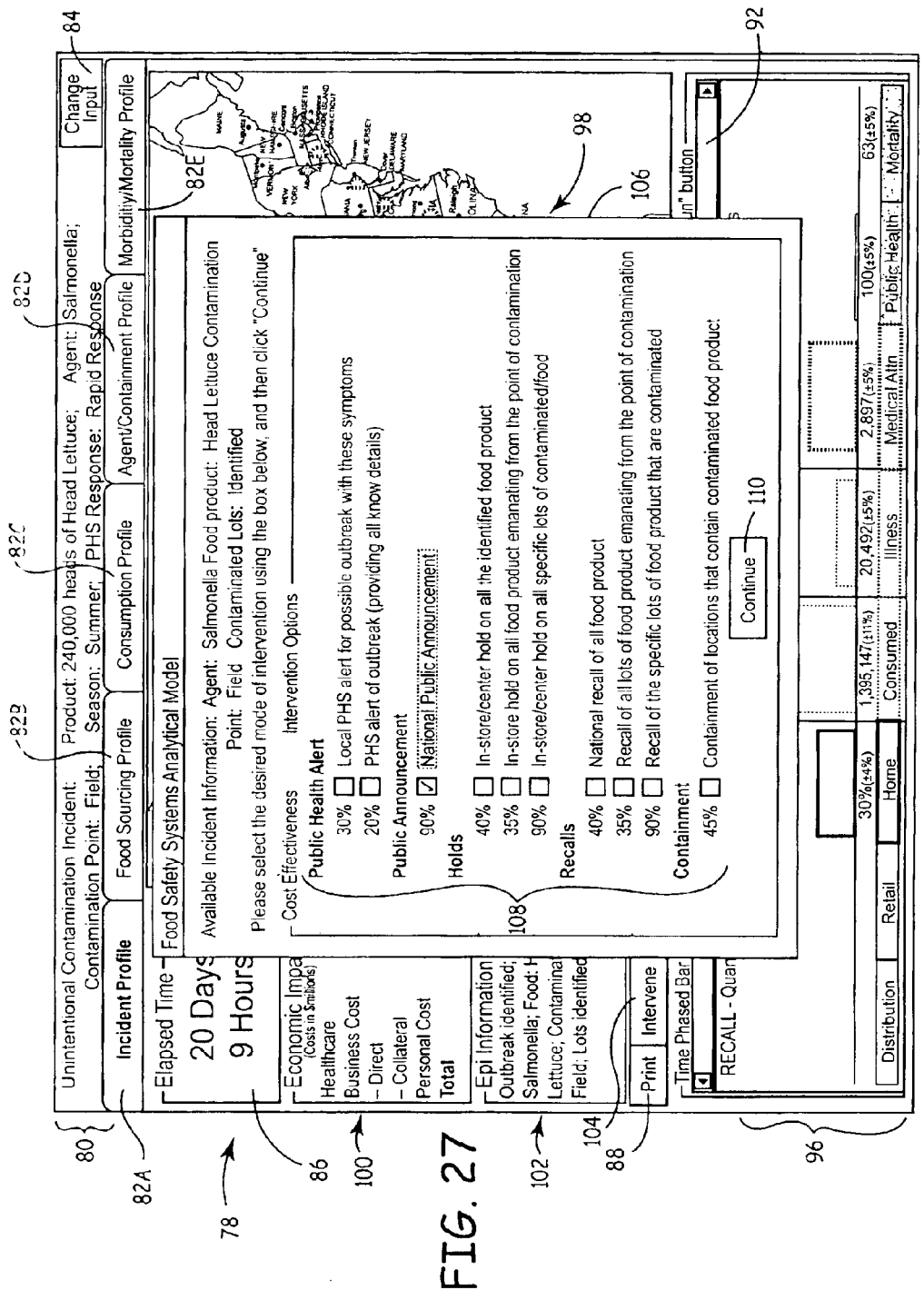

FIGS. 24–26 show the progress of the recall effort. The time phase bar graphs, for example, indicate that 334,977 heads of lettuce remain to be recalled, and as the model progresses, the number remaining to be recalled decreases.

FIG. 26 illustrates the intervention window 106 when the point of contamination is also known (as shown in the epidemiological display 102). Here, the additional intervention options 108 are available, allowing the user to select between multiple options. The intervention options 108 include "public health alerts"; "public announcements" (such as through the media); "product holds" instructing stores to remove product from the shelf and to hold the product; "recalls" of all food product, of all food product issuing from the point of contamination, or of the specific lots of food determined to be contaminated; and "containment". Each intervention option will have morbidity/mortality implications that will be reflected in the illness and death rates, and will have economic implications that will be reflected in the economic display 100. The relative cost effectiveness and the number of options vary as the amount of available information increases.

While additional options are available to the user, it should be noted that the recall option previously selected is now "grayed out", so that the user cannot re-select that option. If the tool 12 were set up to automatically perform selected intervention options, all possible intervention options could be re-presented in order to allow for some overlapping or duplicative intervention options.

Figure 28:
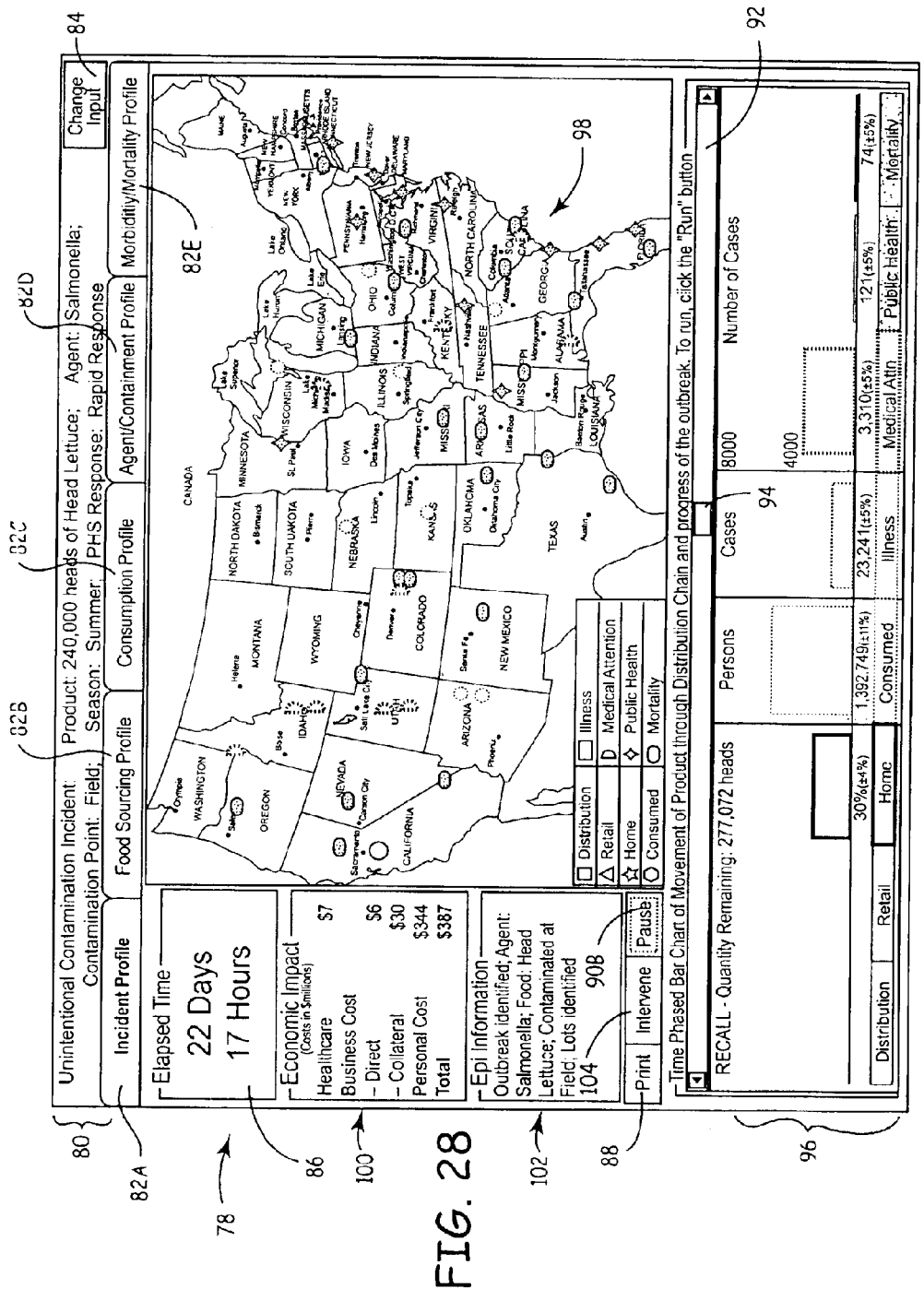

FIG. 28 illustrates the progress of the food incident after selection of the various intervention options. The selected interventions reduce the amount of contaminated product in circulation and prevent some consumers from eating the contaminated product. Thus, as the quantity of product remaining to be recalled continues to decrease (as shown in the time phase bar graph 96), the numbers of people seeking medical attention starts to slow.

Figure 29:
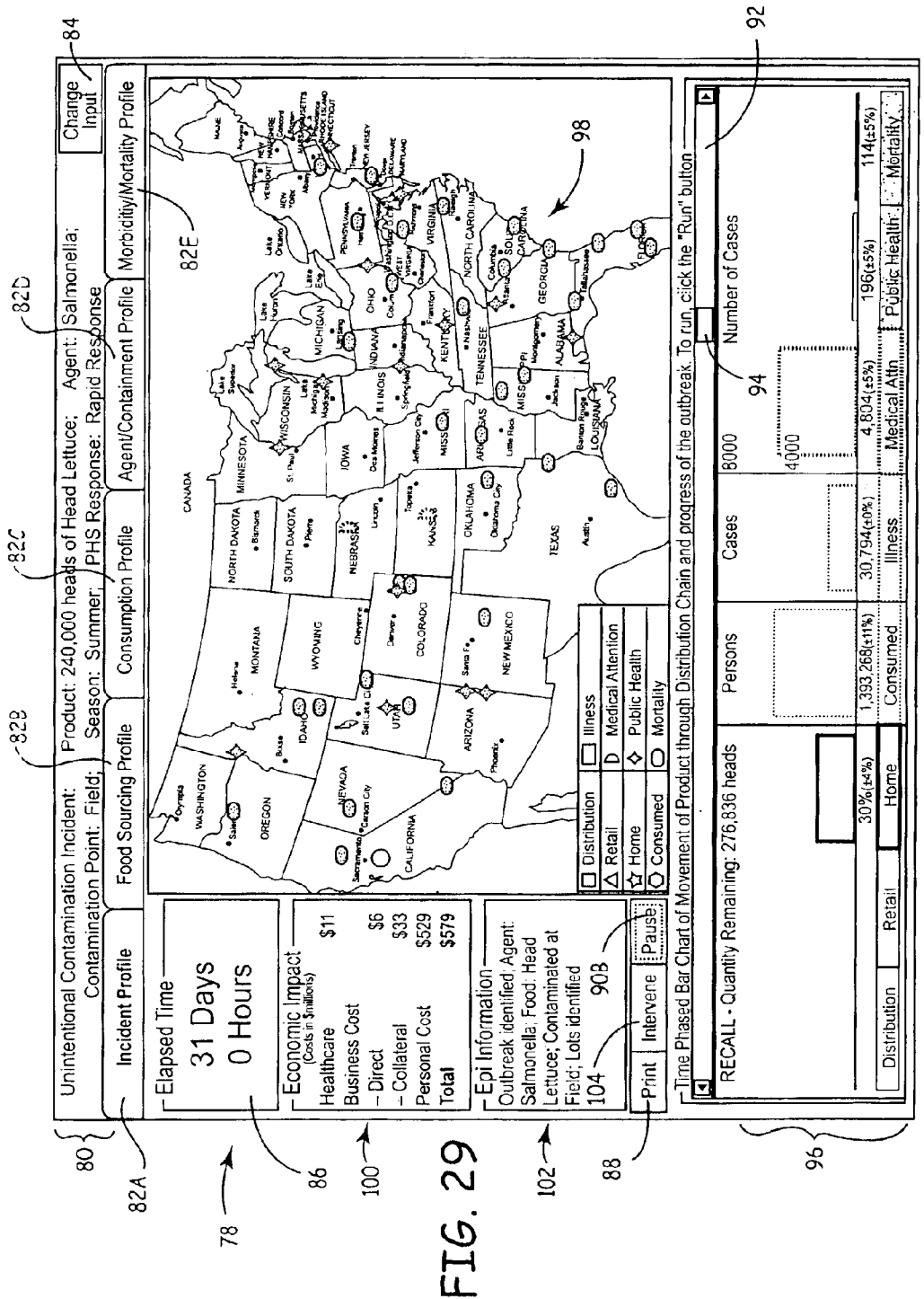
Figure 30:
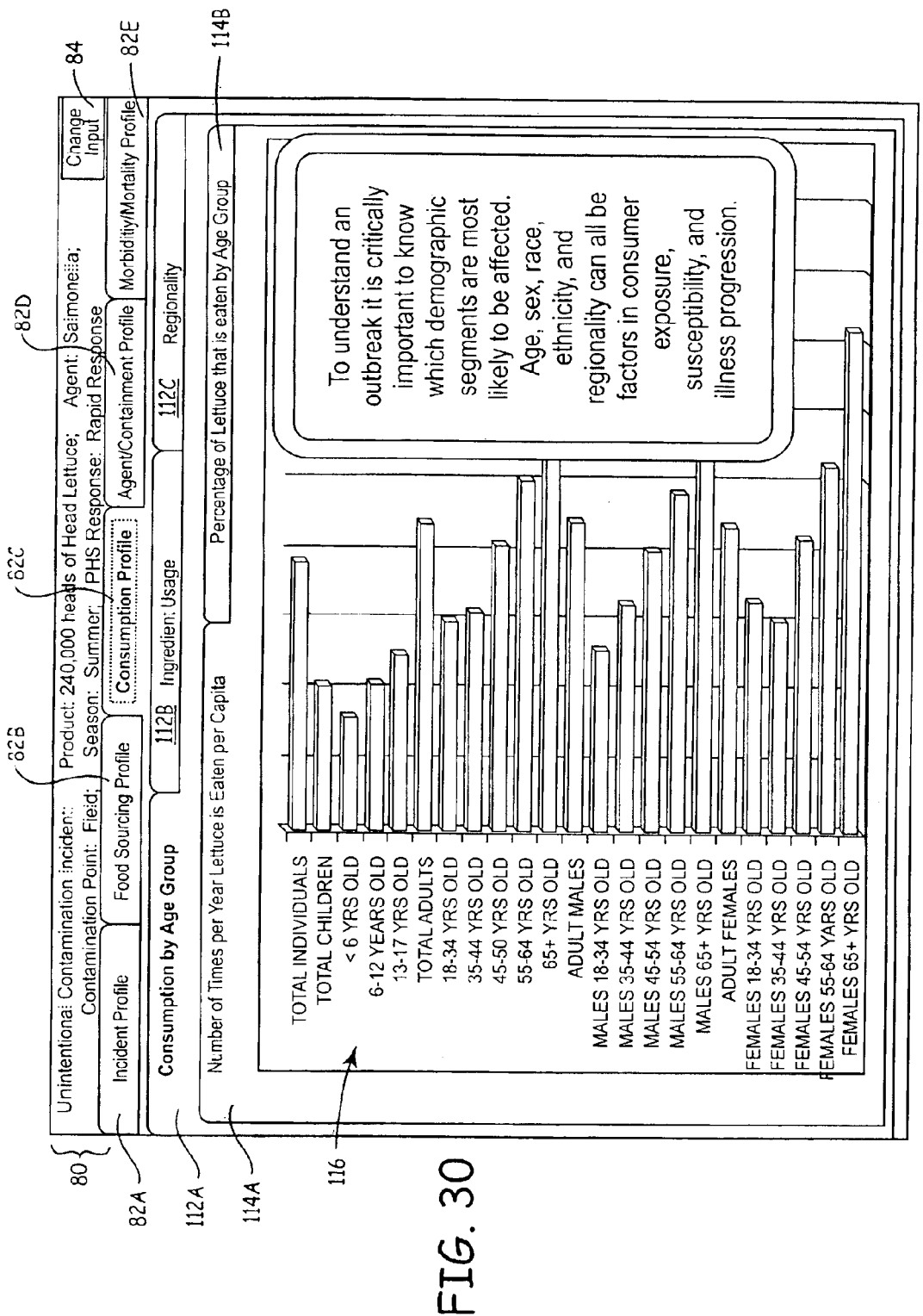
FIG. 30 is a screen shot of the consumption profile information displayed when the "consumption profile" tab is selected by a user, showing the number of times per year lettuce is consumed per capita.

FIG. 29 illustrates the progress of the model at thirty-one days and zero hours. As shown, the economic impact display 100 indicates a total cost of $579 million, and the epidemiological display 102 indicates that the contaminated lots have been identified.

FIG. 29 illustrates the data available to the user via the consumption profile tab 82C. As shown, the tool 12 allows the user to select between tabs within the consumption profile 82C. Specifically, the user can select the consumption by age group tab 112A, the ingredient usage tab 112B, and the Regionality tab 112C. The consumption by age group tab 112A can be further broken down by demographic segments of the population. To fully understand an outbreak, it is critically important to know which demographic segments of the population are most likely to be effected. Age, gender, race, ethnicity, and regionality may all be factors in consumer exposure, susceptibility, and illness progression. Additionally, within this display, the user can select between the number of times this year that the product (here, the product is lettuce) is eaten per capita (tab 114A) and the percentage of lettuce that is consumed for each age group (tab 114B). The tool 12 then assembles and displays the data in a bar chart 116.

Figure 31:
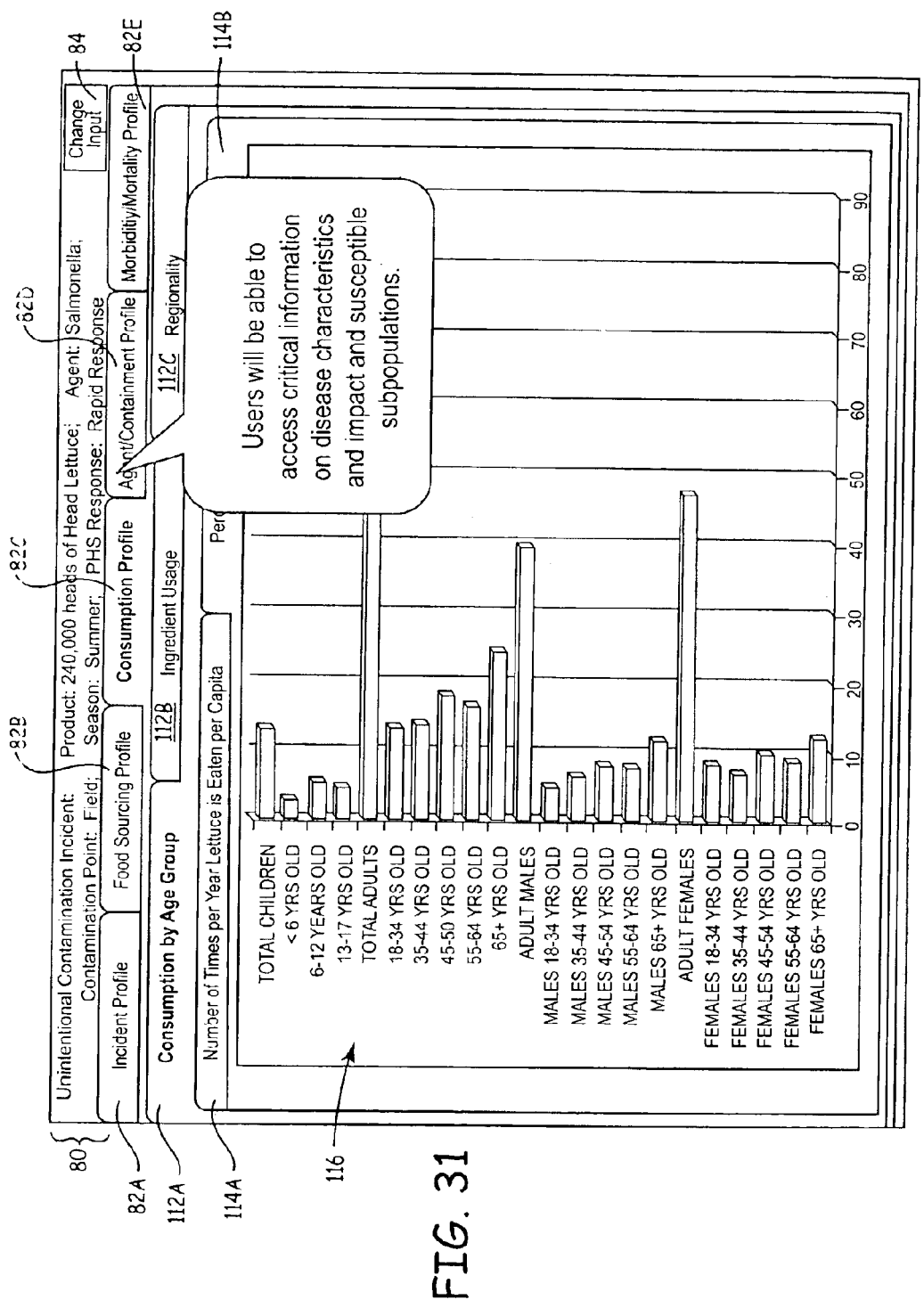
FIG. 31 is a screen shot of the consumption profile information displayed when the "consumption profile" tab is selected by a user and when the "percentage of lettuce consumed by age group" sub category is selected.

As shown in FIG. 31, when tab 114B is selected, the tool 12 displays the percentage of lettuce consumed for each age group. The demographic breakdown provides an additional basis for making intervention decisions, so that users can make intervention decisions based on quantitative and qualitative analysis of the evolving food incident.

In general, the assembly and compilation of food profiles involves the construction of temporal sourcing maps, which illustrate the production centers for products based on actual data from growers/shippers, trade associations and the United States Department of Agriculture (USDA).

It is important to understand that the majority of the preceding discussion has been directed to the tool 12 for analyzing and modeling a food event based on user provided criteria. However, the tool 12 lays the groundwork for a food system that performs in-market food tracking, incident detection and analysis, based on real data and on real time distribution information.

Referring back to FIG. 2, the trace-recall system 30 includes an in-market food tracking system (shown in phantom as element 24), which interacts with the food distribution profiles stored in a database 14A either directly or via a network connection. The in-market food tracking system 24 is a software-based component which may be connected to the network 16 to allow for limited remote access. In general, the In-Market Food Tracking system 24 may occasionally connect to identified links or vendors in the distribution chain via the network 16 (such as the Internet) using a Virtual Private Network (VPN) connection or other secure connection methods as needed to perform a food product trace based on an identified food event.

Specifically, the trace recall system 30 uses an in-market tracking system 24 to perform a one step forward one step back trace of contaminated food product. The recall system 30 may be configured to automatically query existing market databases used and maintained by the identified vendors in the distribution chain (such as retailers, trade associations, wholesalers, and the like) to track products through their own distribution chain. This can be accomplished using secure connections, encryption techniques and/or customized plugins or add-on components. These components can be developed either by the vendor for the particular database or as needed so as to provide an automated, secure interface for interaction between the trace recall system 30 and the individual vendors. Since the interaction will most often occur via a VPN link over the Internet, standard secure Internet interfaces and protocols may be used to connect the two systems, and standard database API can be used for most interactions.

The in-market food tracking system 24 is a database system that allows real time in-market food tracking, enabling immediate "trace forward" of food products to specific retail and food service outlets, as well as "trace back" to the source for the contaminated products. The trace recall system is a searchable database system that links all the members of the food distribution system (farmers, processors/manufacturers, distributors, retail/food service outlets, and the like) making it possible to track specific products from their origin to the point of purchase by consumers.

In the case of a specific food contamination event, the food tracking system 24 interfaces securely with companies using a software system that translates their distribution path data into an accurate, reliable and usable format that can be used by FDA and CDC to identify likely food products implicated in the outbreak and triangulate to help identify the source(s) of the products.

Generally, the system 10 is designed to enable quick, efficient identification and containment of a food contamination event while minimizing the overhead and impact on industry of the development of such systems. When a food contamination incident has evolved to the stage at which the CDC or some other public health agency is able to identify suspected product(s), then the in-market food tracking system 24 may be used to identify the suppliers and to provide contact information for all locations that potentially contain the contaminated food product(s). If desired, the in-market food tracking system 24 can then be used to automatically contact all these locations to inform them of any actions required by the CDC or other public health agency, such as containment or recall.

The in-market food tracking system 24 identifies the distributor(s) and product(s) involved in a contamination incident by comparing the geographic location of incident reports with the known pattern of the food distribution network to triangulate on the specific distributor(s) involved in the incident.

In some embodiments, the trace recall system 30 may include additional elements, such as a Food Pathway Database, a Database Maintenance System and an On-call or on-demand Food Tracing System.

The Food Pathway Database is a database that identifies and links all the various points or links in the food distribution system. This database may be populated with the registration information acquired by the FDA and supplemented with vendor and product information for relevant food items acquired directly from identified links or vendors or companies.

The vendor information is used to link back from each point in the distribution pathway to the previous point (a process referred to as "back tracing"), and the food product list enables the linkages to be specific to each food product. Since current FDA registration regulations exempt restaurants and retailers, it is desirable to obtain the customer lists from the end point of the distribution pathway (the distributors) to point forward to the outlets for the food products, allowing for recall efforts to be as effective as possible.

The Database Maintenance System is used to build and maintain the vendor and product portions of the food pathway database. Since much of the required data must be sourced from the food industry companies, the food tracking system 24 provides three update modes in order to maximize data entry efficiencies and to minimize data input errors:

1) Electronic data capture mode allows for direct input of electronically transmitted data. Companies can use this mode to send data electronically directly from their own systems to food pathway database of the system, via the Internet or other communication means.
2) Internet-based update mode allows for direct entry of the data via an Internet interface. Companies can use this mode to log on to the food tracking system 24 in a secure access mode, and view and update their information in the food pathway database.
3) Batch update mode prompts the vendor to update the information stored in the database. Specifically, the food tracking system 24 periodically sends the vendor or company a copy of its current database information from the food pathway database in either electronic or paper form. The vendor or company then updates this information and returns it to hosts of the system, where the records in the food pathway database can be updated.

The on-demand or on-call trace recall system 30 allows for on-demand food tracing based on the food distribution profiles stored in the food profile database 14A and the food pathway database, or the vendor's databases. The On-call food tracing system 30 operates in two modes:

First, the Incident Detection Mode is used when a contamination of the food supply is suspected, but not confirmed. In this case the locations of suspected contaminations are entered into the food tracing system of the food tracking system 24, which then uses the Food Pathway Database to triangulate these locations to reveal their common distribution pathways and the types of products handled on those pathways.

Triangulating the locations of the suspected contaminations with the pathways stored in the pathway database, the system 10 can be used to generate key information to help identify the likely source of the contamination, i.e. the contaminated food product.

Additionally, this type of information enables epidemiological studies (and also possibly FDA requests for food records) to be focused on only those facilities that are linked to the suspected locations. Specifically, for each food product, specific distributors may be identified based on the various locations of people exhibiting symptoms of food based illness. Once the specific distributor is located, the contaminated product can be traced and recalled as necessary.

The other mode in which the system 10 operates is the food trace mode, which is used when a contamination of the food supply is confirmed and a containment or recall action is to be taken. In this instance, it is important to identify the actual locations where the contaminated product is located, so that the recall/containment effort can be focused on the actual sites affected. This focus is particularly significant if the contaminant has possible residual effects (such as with bio-toxins such as Anthrax, which tends to contaminate storage locations) so that decontamination of the affected sites can be facilitated.

To identify the actual location of affected product requires detailed information of day-to-day product shipments, but the burden on industry to maintain and provide such information could potentially be considerable. To minimize this burden the food tracking system 24 uses an "on-call" or on-demand approach that requires detailed shipment information to be collected only when an actual contamination event occurs.

As previously mentioned, each vendor keeps its own information relating to its product distribution up and down stream. The databases of vendors who sell into areas where the suspected contaminations have occurred can be queried automatically to collect the required information only from those companies that are in the distribution pathway of the contaminated product. Limiting the information requests on this basis reduces the frequency of information requests and also reduces the number of companies affected by each request. Since the system performs the triangulation and identifies the potential sources automatically, the limited data gathering can be performed with no loss of system effectiveness.

When a contamination of a food product is confirmed and a containment or recall action is required, the trace recall system 30 is initiated by entering the location and timing of reports of contamination. The food tracking system 24 uses the data to triangulate to identify all distributors who ship the implicated food product to ALL the locations of reported contamination. The system 24 then requests detailed information of day-to-day shipments from implicated vendors. This information is used to generate a list of all outlets that have received the contaminated product. Additionally, if desired, a requesting public health agency, such as the CDC, can notify the system 10 of the recall/containment action that is required, and the system 10 will forward this notification to all locations that potentially contain contaminated product.

For such an on-call system to work efficiently, it is essential that the data collected from the various companies be complete, compatible and internally consistent. Absent a certain level of accuracy, the information from one company will not match that from others in the distribution path, and the integrity of the entire process may be compromised. Resolving such errors would require reformatting and data conversion, activities that, if performed under the pressure of a food contamination event, would be difficult and would inevitably lead to errors and time delays.

To avoid such complications, the food tracking system 24 includes a process that ensures that participating companies will achieve the required data integrity before the data is actually needed. This process has four steps.

First, a standard for Trace data can be instituted industry-wide. This standard should be a comprehensive specification for the content and format of the data required.

Second, the standard must be implemented in existing and new software products. Many companies in the food industry already maintain the data required for the On-call Food Tracing System 30 on software systems purchased from external software vendors. Some such software vendors would participate in developing the standards, and those software vendors that did not participate in the development of the standards will be contacted, informed of the standard and encouraged to develop an interface that will extract the required data sets from their systems (standard data sets will be provided for validation purposes).

Third, the various trade associations and vendors must adopt the standard. If the government imposes such standards, all companies that are subject to the regulations will be contacted, informed of the existence of the regulations and the standard for their implementation, and requested to participate in the On-call Tracing System 30. Those companies that agree to participate will be assisted as necessary to implement the required changes to their systems.

Finally, conformance of the extracted data will be validated. To that end, the final step of the process requires each participating company periodically submit data sets from their systems to ensure that the implementation has been successful. Companies that complete the periodic validation process will be issued a certificate of conformance with the standard.

Generally, the food tracking system 24 of the present invention provides numerous advantages. First, the food tracking system 24 facilitates detection, containment and recall of any product involved in a food contamination event with:

1) Faster detection of wide spread food incidents, by identifying when geographically separated reports are linked through the distribution process;
2) Faster and more accurate detection of the food item responsible for a contamination incident, by isolating the food items that correlate with reported locations of contamination;
3) Sharper focus of containment or recall notifications, as these can be focused only on the specific locations that are potentially involved in the event, hence reducing the impact on locations that are not involved;
4) Faster and simpler recall/containment actions, as the required information is instantly accessible from a single source of contact;
5) Minimizes impact on industry, by reducing the frequency and scope of data submissions; and
6) Ensures integrity of the data collection process, by setting standards for the data to be submitted and facilitating the implementation of these standards throughout industry.

The gathered data provides the CDC or other public health agency limited access to "one forward—one back" detailed shipment information so that only those companies involved in the relevant distribution pathway are contacted in the event of a recall. More importantly, contaminated food items can be traced from any known source forward and backward to render any such recall effort more efficient.

Thus far, the tools discussed will allow a faster route to identification of suspected food products and sources, limit containment and remediation to specific companies and geographies, and reduce consumer exposure and collateral damage to food companies. Additionally, these tools will facilitate industry's compliance with the record keeping requirements portion of the Bioterrorism Preparedness and Response Act of 2002.

Finally, an early detection system (not shown) may be implemented as an additional or supplemental component to the system 10. The early detection system would include a data capture interface, databases, and symptom information for authorized users. Generally, the goal would be to provide an interface for public health officials and doctors to enter information early in a contamination incident, such as where persons who experience early symptoms of a food event could be expected, such as: 1) those who are likely to have early exposure to a contaminating agent (for example workers in the food production chain, including growers, manufacturers, distributors and retailers); and 2) those who are likely to have early reaction to consumption of a contaminated food (for example, persons who are likely to consume food during preparation such as personnel at restaurants, fast food outlets) and persons that are most likely be symptomatic quickly after exposure (young children).

Potential "canary sites are identified by using the food tracking system database for identifying contacts in the food industry and by using public records for making health personnel contacts in schools. As sites are identified, contacts are developed by email (if available) or by phone both to establish who is the appropriate contact and to enlist the cooperation of the contact. For example, in a food company, the initial contact can be made in the Employee Relations department or equivalent office; in a school the initial contact can be the school nurse or equivalent.

The employee contact will be contacted, informed of how the data capture system early warning system works, and asked if he or she will cooperate in becoming part of the data capture system ("early warning system") by agreeing to fill in a short 'Survey' report each time they become aware of any unusual illness in their immediate environment that may be indicative of a possible food incident. If he or she agrees to cooperate, he or she is instructed to access the Internet web site (interface) of the data capture system, and to set register a user identity and password and to enter an email address on the site. The data capture system "walks" the user through an automatic, online demonstration that teaches the user the types of symptoms that should be reported through the data capture system, and how to use the data capture system to enter the required reports.

Thereafter, any time that the user become aware of any unusual illness in his or her immediate environment, he or she visits the web site and fills in a brief report with information that will help to identify a food event. Each report contains an identification of the contaminated individual (e.g. Employee number or student number); Age; Sex; Symptoms (from a list); Person's Condition and Timing of Symptoms (how long since the first symptom, etc). This report is forwarded (e-mailed or entered directly) in real-time into the data capture system, which automatically analyzes the report within the context of all other reports that it has received to determine if this report is possibly linked to a food contamination event. If such a linkage is suspected then the data capture system contact is informed of the possibility that the reported event is in fact food related. The system can also inform the user of appropriate follow-up actions, such as acquiring additional information to confirm the existence of the event, or recommending additional patient care.

The data capture system may receive ongoing information from external systems of evidence of any food event that is underway. When there is evidence that an existing food event may affect one or more canary sites, the data capture system contacts are informed by email of the suspected event and of the probable symptoms of the event with a warning to be on the watch for additional cases.

To ensure that the registered "canary site" contacts have a continuing participation and feeling of reward from their involvement, the contacts are automatically advised of all food warnings and recalls that are issued, and receive monthly reports by email summarizing the activity and other relevant and interesting information from the previous month associated with the data capture system.

It is understood that Internet-based systems are inherently vulnerable, and that the vendors would be supplying sensitive information to the system. Thus, system components that are connected to the Internet should not contain information in a form that would compromise the trust of cooperating vendors or companies.

By definition, any network connected to the Internet (no matter the security precaution) is unsecure. Therefore, all reasonable security precautions have been implemented on those exposed systems.

Since it is assumed that the exposed systems are unsecure (by definition), as an additional security measure, no confidential data is stored in the profile database 14A or the food tracking system 24 (as explained below). Moreover, the only physical connection between the Internet-accessible systems and internal development systems is a LAN connection that is plugged in only for the brief time required for data transfers between systems, and after the transfers are made the connection is severed. By limiting connections between the internal networks and the internal development systems at the physical layer, the development systems are virtually impervious to hacking.

For the Food Profiles, all raw data is actually processed on the development systems, and the only data accessible through the Internet systems is the statistical averages, for which the confidentiality concerns are sufficiently low that the data can reasonably be exposed on the Internet.

In the food tracking system 24, the lot-by-lot data is collected only at the time of an outbreak, so there is no large historical database to cause a security concern. The only significant database that allows for access over the Internet is the "Food Pathway Database", which contains information on each company in the food system and the linkages between these companies. However, access to the food pathway database is severely limited via firewall and other security measures. In fact, access to the food pathway database may be restricted to queries directed from a particular IP address or from a web-page, so as to inhibit unauthorized access.

Generally, as described above, the food pathway database is accessed only in the event of an outbreak, and is used for triangulation purposes. Access to the food pathway database may be provided only through email queries indicating sites that have reported contamination, and then the response can be generated as an email message. Alternatively, when the system 10 receives a triangulation request, the system can generate a subset of the main database that contains only the relevant data on companies that are potentially implicated. This subset database could then be secured with new passwords and exposed over the Internet only to the person who initiated the request through a secure VPN. When the outbreak is over the subset database and VPN will be erased.

Generally, the system 10 presented above illustrates an embodiment of the present invention. Specific elements of the invention, such as the expert system, could be implemented on the same network or on different networks and systems. Various components could be integrated into a single system or divided into multiple systems, depending on the particular implementation.

Additionally, while the present invention has been described largely with respect to food product contamination and recall, the same system could be adapted to provide a similar service for pharmaceutical and other products; however, the particular discriminants for the purpose of designing the product profiles would need to be adjusted to accurately profile the purchase and consumption of products that have a longer shelf life.

Although the present invention has been described with reference to preferred embodiments, workers skilled in the art will recognize that changes may be made in form and detail without departing from the spirit and scope of the invention.

What is claimed is:

1. A method for modeling a product contamination incident, the method comprising:
   receiving a product type to be modeled, the product type associated with product distribution data stored in a distribution database;
   receiving a response time value related to an expected amount of time before a health department is made aware of the contamination incident; and
   modeling statistically the product contamination incident as an evolving contamination event.

2. The method of claim 1 wherein the step of receiving the product type comprises:
   providing a user interface that is linked to the distribution database, the user interface adapted to receive the product type.

3. The method of claim 1 wherein the step of receiving the response time comprises:
   providing a user interface that is linked to the distribution database, the user interface adapted to receive the response time.

4. The method of claim 3, wherein the response times are slow response, normal response, or fast response.

5. The method of claim 3 wherein the response time is a numeric value representative of a unit of time.

6. The method of claim 3 wherein the response time is a value entered by a user that is representative of a unit of time.

7. The method of claim 1 wherein before the step of receiving, the method further comprising:
   compiling a distribution profile corresponding to a flow of a product over time within a stream of commerce, each product having an associated distribution profile; and
   storing each distribution profile according to its product type within the distribution database.

8. The method of claim 1 and further comprising: offering context-based intervention options for responding to the evolving contamination event.

9. The method of claim 8 wherein the intervention options are based on available information and a volume of product at each stage of a distribution chain according the evolving contamination event.

10. The method of claim 8 and further comprising:
    aggregating an estimated health cost associated with the evolving contamination incident.

11. The method of claim 10 and further comprising:
    providing a user interface adapted display the intervention options and to receive a user selection from the displayed intervention options; and
    mitigating the health cost based on the user selection.

12. The method of claim 1 wherein the step of modeling comprises:
    calculating over time a probable distribution of product within a stream of commerce based on information stored in the product distribution database;
    estimating a probable distribution of contamination incidents based on the calculated distribution of product;
    estimating a time at which health officials become aware of the contamination incident based on the response time value; and
    calculating over time a probable health cost associated with the contamination event beginning at the time at which health officials become aware of the contamination incident.

13. A system adapted to model a product contamination incident, the system comprising:

a product distribution database containing distribution data related to a flow of products in a stream of commerce, the distribution data being related to particular products;

a modeling software system adapted to receive a selected contamination type and a selected product type, and to model a probable contamination incident distribution within a stream of commerce based on the distribution data and on the selected contamination type and the selected product type; and a user interface adapted to display the distribution data to provide user interaction options to a user.

14. The system of claim 13 and further comprising:

a food tracking system adapted to identify a source for a contaminated product, the food tracking system adapted to relate geographically related contamination events to specific suppliers of the product within a geographic area of the contamination event; and a trace system adapted to trace a product within a product distribution chain, the trace system adapted to link a contaminated product with a source and adapted to track all contaminated products deriving from the source.

* * * * *